(12) United States Patent
Binmoeller et al.

(10) Patent No.: US 10,722,341 B2
(45) Date of Patent: Jul. 28, 2020

(54) BILIARY STENTS AND METHODS

(71) Applicant: Boston Scientific Scimed, Inc., Maple Grove, MN (US)

(72) Inventors: Kenneth F. Binmoeller, San Francisco, CA (US); Sieu T. Duong, Hayward, CA (US); Hanh H. Duong, Hayward, CA (US); Thao Nguyen, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 16/009,619

(22) Filed: Jun. 15, 2018

(65) Prior Publication Data
US 2018/0289463 A1 Oct. 11, 2018

Related U.S. Application Data

(63) Continuation of application No. 14/743,191, filed on Jun. 18, 2015, now abandoned.

(60) Provisional application No. 62/013,908, filed on Jun. 18, 2014.

(51) Int. Cl.
| | | |
|---|---|---|
| *A61F 2/04* | (2013.01) | |
| *A61F 2/82* | (2013.01) | |
| *A61F 2/07* | (2013.01) | |
| *A61F 2/90* | (2013.01) | |

(52) U.S. Cl.
CPC .............. *A61F 2/04* (2013.01); *A61F 2/07* (2013.01); *A61F 2/90* (2013.01); *A61F 2002/041* (2013.01); *A61F 2230/001* (2013.01); *A61F 2230/0069* (2013.01); *A61F 2230/0095* (2013.01); *A61F 2250/0019* (2013.01)

(58) Field of Classification Search
CPC ...... A61F 2/04; A61F 2/07; A61F 2/82; A61F 2/90
USPC .................................................. 623/1.3–1.32
See application file for complete search history.

(56) References Cited

U.S. PATENT DOCUMENTS

| | | | | |
|---|---|---|---|---|
| 5,425,739 | A * | 6/1995 | Jessen ................... | A61B 17/11 606/153 |
| 5,645,559 | A | 7/1997 | Hachtman et al. | |
| 8,323,350 | B2 * | 12/2012 | Nissl ....................... | A61F 2/04 623/1.15 |

(Continued)

FOREIGN PATENT DOCUMENTS

| | | |
|---|---|---|
| CN | 2899736 | 5/2007 |
| CN | 2910150 | 6/2007 |

(Continued)

OTHER PUBLICATIONS

Communication pursuant to Article 94(3) for Application No. 15734495.3, dated Mar. 11, 2019, 7 pages.

(Continued)

*Primary Examiner* — Suzette J Gherbi

(57) ABSTRACT

A tissue lumen stent is provided with a body having an elongated tubular configuration and a foreshortened configuration. In the foreshortened configuration, downstream and upstream ends of the body expand radially into downstream and upstream flange structures, leaving a generally cylindrical saddle region therebetween. In some embodiments, the flange structures are non-symmetrical with respect to one another. Systems and methods of using the stents are also disclosed.

20 Claims, 13 Drawing Sheets

(56) References Cited

U.S. PATENT DOCUMENTS

| | | | |
|---|---|---|---|
| 9,668,853 B2 | 6/2017 | Shin | |
| 10,278,841 B2* | 5/2019 | Clerc | A61F 2/90 |
| 10,327,778 B2* | 6/2019 | Weiner | A61F 2/04 |
| 2006/0259113 A1* | 11/2006 | Nissl | A61F 2/04 623/1.3 |
| 2006/0276887 A1* | 12/2006 | Brady | A61F 2/90 623/1.53 |
| 2007/0179590 A1* | 8/2007 | Lu | A61F 2/07 623/1.16 |
| 2009/0143713 A1 | 6/2009 | Van Dam et al. | |
| 2009/0157158 A1 | 6/2009 | Ondracek et al. | |
| 2009/0326431 A1* | 12/2009 | Heise | A61F 2/06 604/8 |
| 2013/0274685 A1* | 10/2013 | Jordan | A61F 2/95 604/264 |
| 2013/0325143 A1* | 12/2013 | Lamson | A61F 2/82 623/23.66 |
| 2014/0074065 A1* | 3/2014 | Muni | A61L 31/06 604/514 |
| 2014/0243950 A1* | 8/2014 | Weiner | A61F 2/04 623/1.12 |
| 2014/0257466 A1* | 9/2014 | Board | A61F 2/2403 623/2.11 |
| 2015/0045908 A1* | 2/2015 | McMahon | A61F 2/04 623/23.68 |
| 2016/0081832 A1* | 3/2016 | Hingston | A61F 5/0076 623/23.65 |
| 2016/0135941 A1* | 5/2016 | Binmoeller | A61F 2/04 623/23.7 |
| 2016/0151146 A1* | 6/2016 | Walak | A61F 2/848 623/23.7 |
| 2016/0158040 A1* | 6/2016 | Zupkofska | A61F 2/82 623/23.7 |
| 2016/0175123 A1* | 6/2016 | Walsh | A61F 2/04 623/23.7 |
| 2016/0175125 A1* | 6/2016 | Brady | A61F 2/90 623/23.7 |
| 2016/0175126 A1* | 6/2016 | Walsh | A61F 2/04 623/23.7 |
| 2016/0242893 A1* | 8/2016 | Joshi | A61F 2/01 |
| 2016/0262881 A1* | 9/2016 | Schankereli | A61F 2/2418 |
| 2018/0185183 A1* | 7/2018 | Christakis | A61F 2/966 |
| 2018/0289463 A1* | 10/2018 | Binmoeller | A61F 2/04 |
| 2019/0053901 A1* | 2/2019 | Racchini | A61F 2/2418 |

FOREIGN PATENT DOCUMENTS

| | | |
|---|---|---|
| CN | 201668549 | 12/2010 |
| CN | 201879873 | 6/2011 |
| CZ | 303606 B6 | 1/2013 |
| EP | 1795151 A1 | 6/2007 |
| JP | 55161539 U | 11/1980 |
| JP | H07502673 A | 3/1995 |
| WO | 2007079153 A2 | 7/2007 |

OTHER PUBLICATIONS

Binmoeller, K.F., and Shah, J., "A novel lumen-apposing stent for transluminal drainage of nonadherent extraintestinal fluid collections", Endoscopy 43:337-342 (2011).

Binmoeller et al., "A Kit for EUS-Guided Access and Drainage of Pancreatic Psuedocysts: Efficacy in a Porcine Model" Spring Publishing, vol. 1 Issue 3, Nov. 14, 2012, 6 pages.

Binmoeller et al., "A novel lumen-apposing stent for transluminal drainage of nonadherent extraintestinal fluid collections" Jan. 24, 2011, Endoscopy 2011; 43; 337-342 © George Thieme Verlag KG Stuttgart—New York.

Binmoeller et al., "Endoscopic ultrasound-guided gastroenterostomy using novel tools designed for transluminal therapy: a porcine study" Endoscopy 2012; 44: 499-503 © George Thieme Verlag KG Stuttgart—New York.

\* cited by examiner

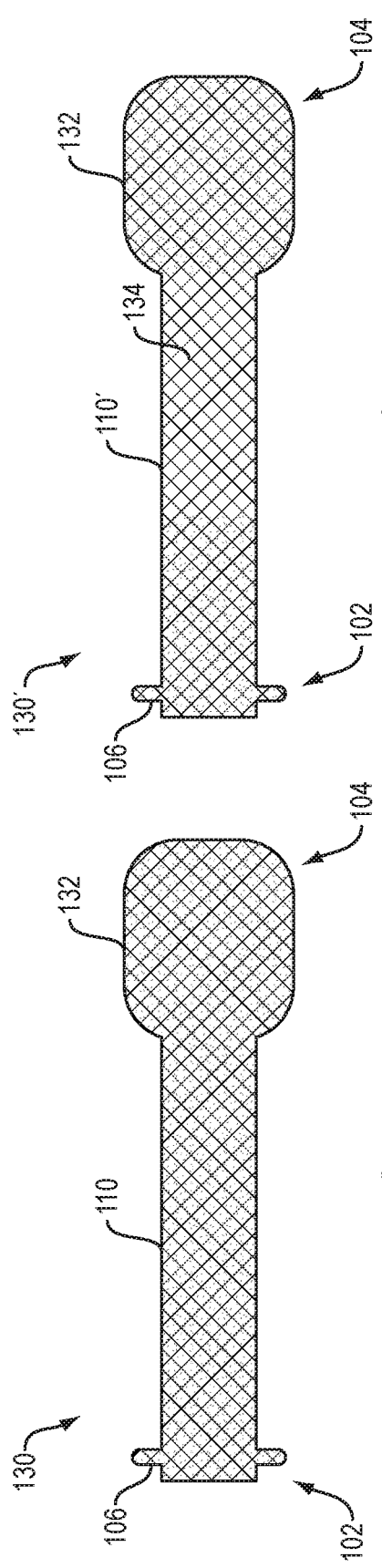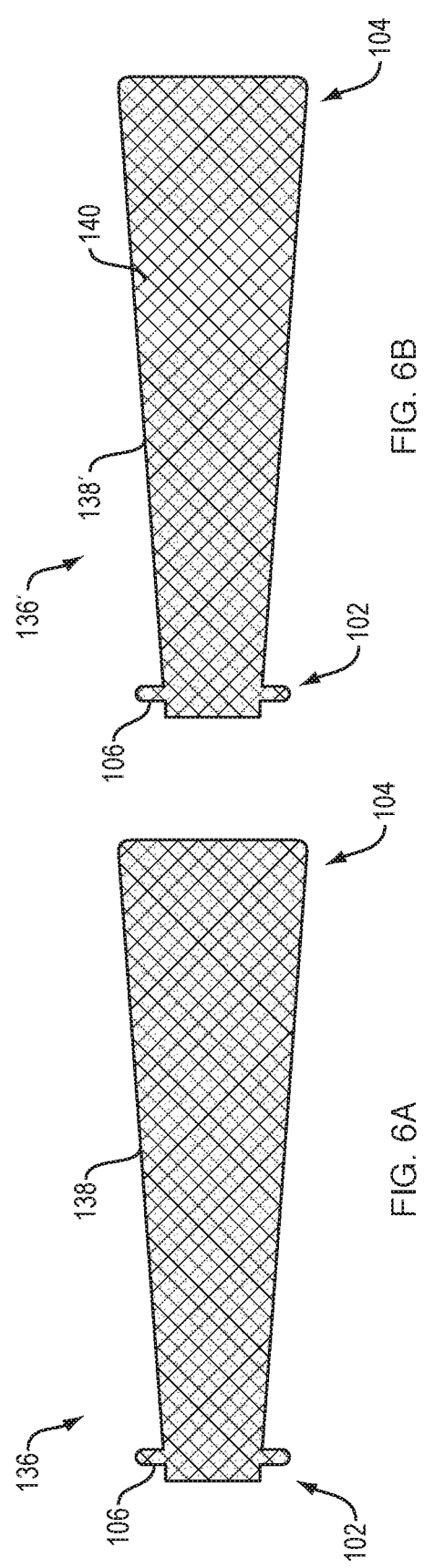

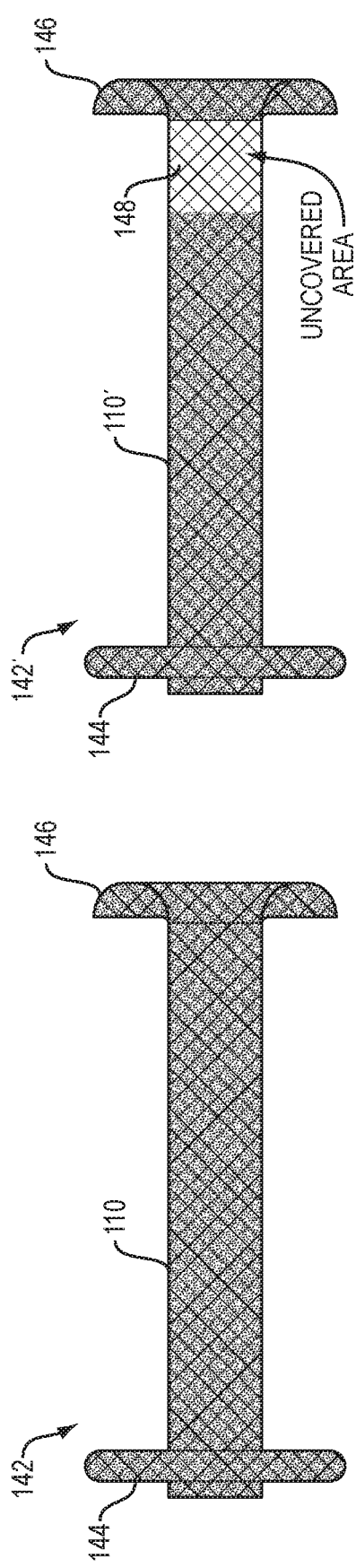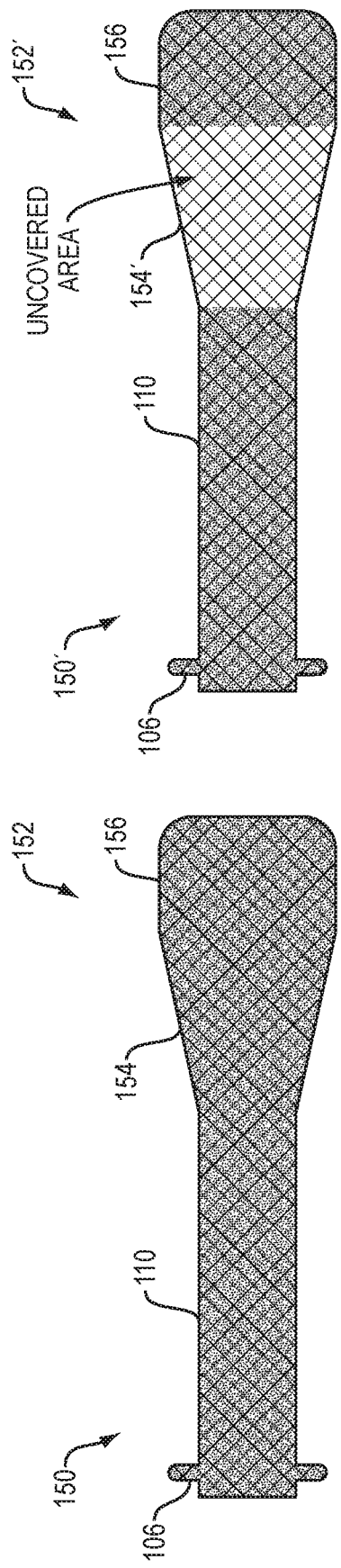

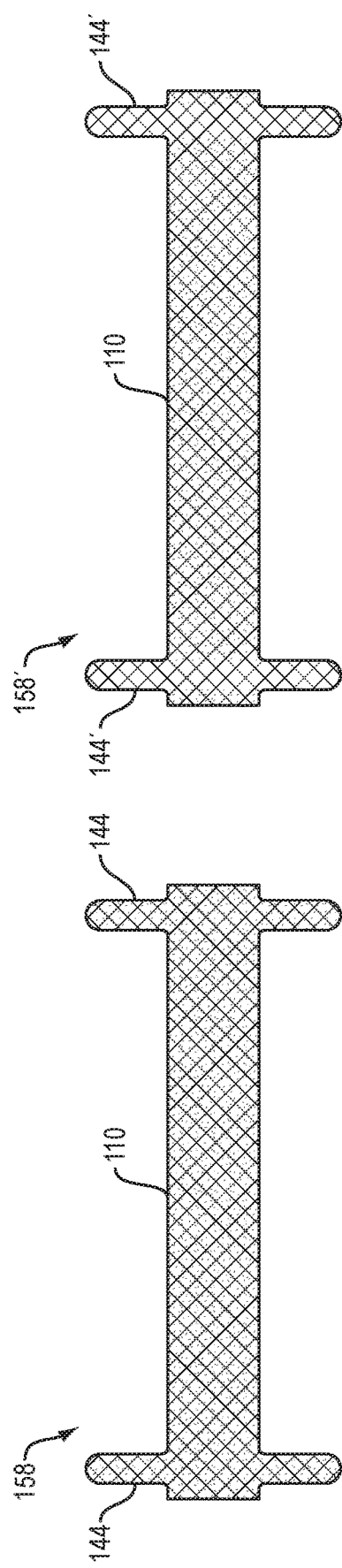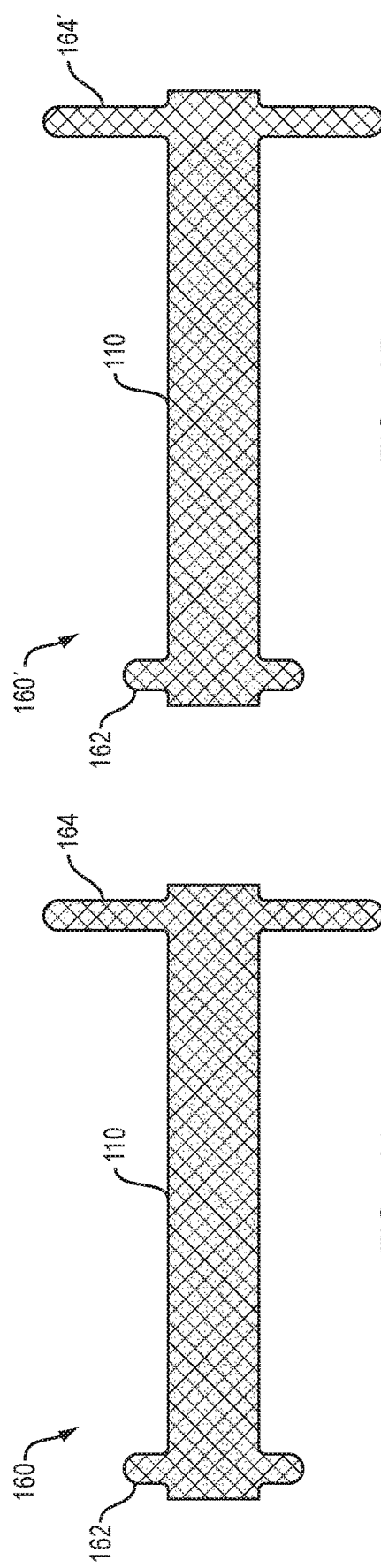

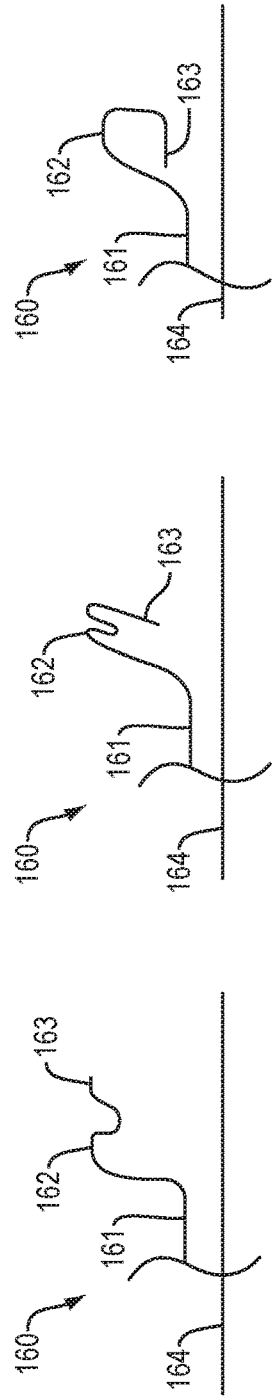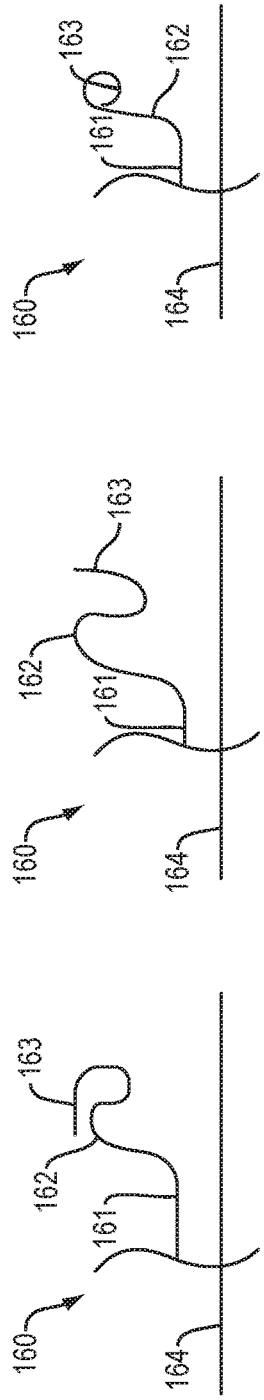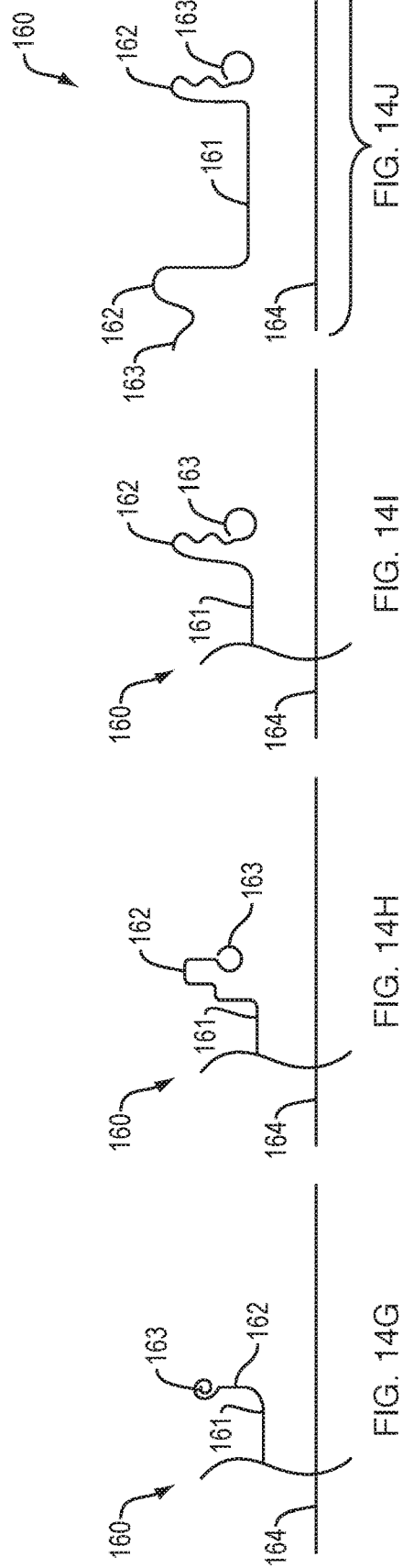

BILIARY STENTS AND METHODS

CROSS-REFERENCE TO RELATED APPLICATIONS

This application is a continuation of, and claims the benefit of priority to, U.S. patent application Ser. No. 14/743,191, filed Jun. 18, 2015, which claims the benefit of priority to U.S. Provisional Patent Application Ser. No. 62/013,908 by Binmoeller, et al. titled "Biliary Stents and Methods" and filed Jun. 18, 2014. The foregoing patent application and all publications and patent applications mentioned in this specification are incorporated by reference herein to the same extent as if each individual publication or patent application was specifically and individually indicated to be incorporated by reference. For example, this application incorporates by reference in its entirety U.S. Patent Publication Nos. 2009/0281557 and 2013/0310833.

FIELD

This application relates generally to medical methods and devices. More specifically, the present disclosure relates to lumen stents and methods for their use in maintaining lumen patency with medical procedures.

SUMMARY OF THE DISCLOSURE

The various aspects of this disclosure relate generally to lumen stents and methods for their use in maintaining lumen patency with medical procedures. In one aspect, the present disclosure relates to a tissue lumen stent having a body with upstream and downstream ends and a region therebetween, which has an elongated tubular configuration and a foreshortened configuration in which the upstream and downstream ends expand radially into flanged structures while the region therebetween is generally cylindrical. In some cases, when the stent is in the foreshortened configuration, the upstream flange structure has a larger maximum lateral dimension, axial width and/or axial radius than that of the downstream flange structure, and may include an inclined portion having an axial length at least as long as a maximum diameter of the saddle region when the body is in the foreshortened configuration. On the other hand, some embodiments are characterized by a downstream flange structure that has a larger maximum lateral dimension, axial width and/or axial radius than that of the upstream flange structure. Alternatively or additionally, the upstream flange structure can include a distal-most opening having a diameter larger than a maximum internal diameter of the saddle region when the body is in the foreshortened configuration. In certain embodiments, the body includes a covered mesh, and in some cases, may comprise both covered and uncovered mesh, while some embodiments include a covering or membrane over at least the cylindrical saddle portion of the stent and, optionally, one or both of the upstream and downstream flange structures.

In another aspect, the present disclosure relates to a tissue lumen stent comprising a body having an elongated tubular configuration and a foreshortened configuration in which a downstream end of the body expands radially into a downstream flange structure and an upstream end of the body expands into a distally and radially outward inclined structure. The body of the stent upstream of the downstream flange structure optionally increases in diameter (or tapers) in a continuous manner toward the upstream end. The upstream and downstream flange structures are optionally non-symmetrical, and as described above, the upstream flange structure has a larger maximum lateral dimension, axial width and/or axial radius than that of the downstream flange structure, and may include an inclined portion having an axial length at least as long as a maximum diameter of the saddle region when the body is in the foreshortened configuration. In some cases, the upstream and downstream flange structures are substantially symmetrical in the extended configuration. The stent optionally includes a covering or membrane over the cylindrical saddle portion, which can extend over one or both of the upstream and downstream flanges. In some instances, the upstream and/or downstream flange structures have a pull-out force greater than about 2.49 N.

In yet another aspect, the disclosure relates to a method of treating a patient using a tissue lumen stent as described above. The method generally includes the steps of (a) accessing a biliary system of a patient with an endoscope, and (b) deploying, within the biliary system of the patient, a tissue lumen stent with a foreshortened configuration defining non-symmetrical upstream and downstream flange structures and a cylindrical portion extending between them. The method optionally includes contacting a lumen such as the common bile duct, the pancreatic duct, and the hepatic duct.

BRIEF DESCRIPTION OF THE DRAWINGS

Novel features of the invention are set forth with particularity in the claims that follow. A better understanding of the features and advantages of the present invention will be obtained by reference to the following detailed description that sets forth illustrative embodiments, in which principles of the invention are utilized, and the accompanying drawings (which are not necessarily shown to scale) of which:

FIGS. 5A-10B are enlarged lateral views of additional exemplary stents.

FIGS. 14A-14J illustrate cross sections of stents in accordance with some embodiments.

DETAILED DESCRIPTION

The present disclosure uses the terms anterograde, retrograde, downstream, upstream, proximal, distal, lower, upper, inferior and superior to refer to various directions. Unless the context clearly indicates otherwise, the terms anterograde, downstream, proximal, lower, and inferior will generally be used synonymously to indicate a direction that is in line with fluid flow and along the devices and instruments toward the surgeon. Conversely, the terms retrograde, upstream, distal, upper and superior will generally be used synonymously to indicate a direction that is against fluid flow and along the devices and instruments away from the surgeon. It should be noted, however, that this nomenclature is being defined here to help clarify the following descriptions rather than to limit the scope of the invention. While the exemplary embodiments disclosed herein focus on entry and placement in a retrograde direction, the disclosed methods, systems and devices may in some circumstances be placed in an anterograde direction. In such situations, the "upstream" and "downstream" designations may be reversed.

Figure 1:
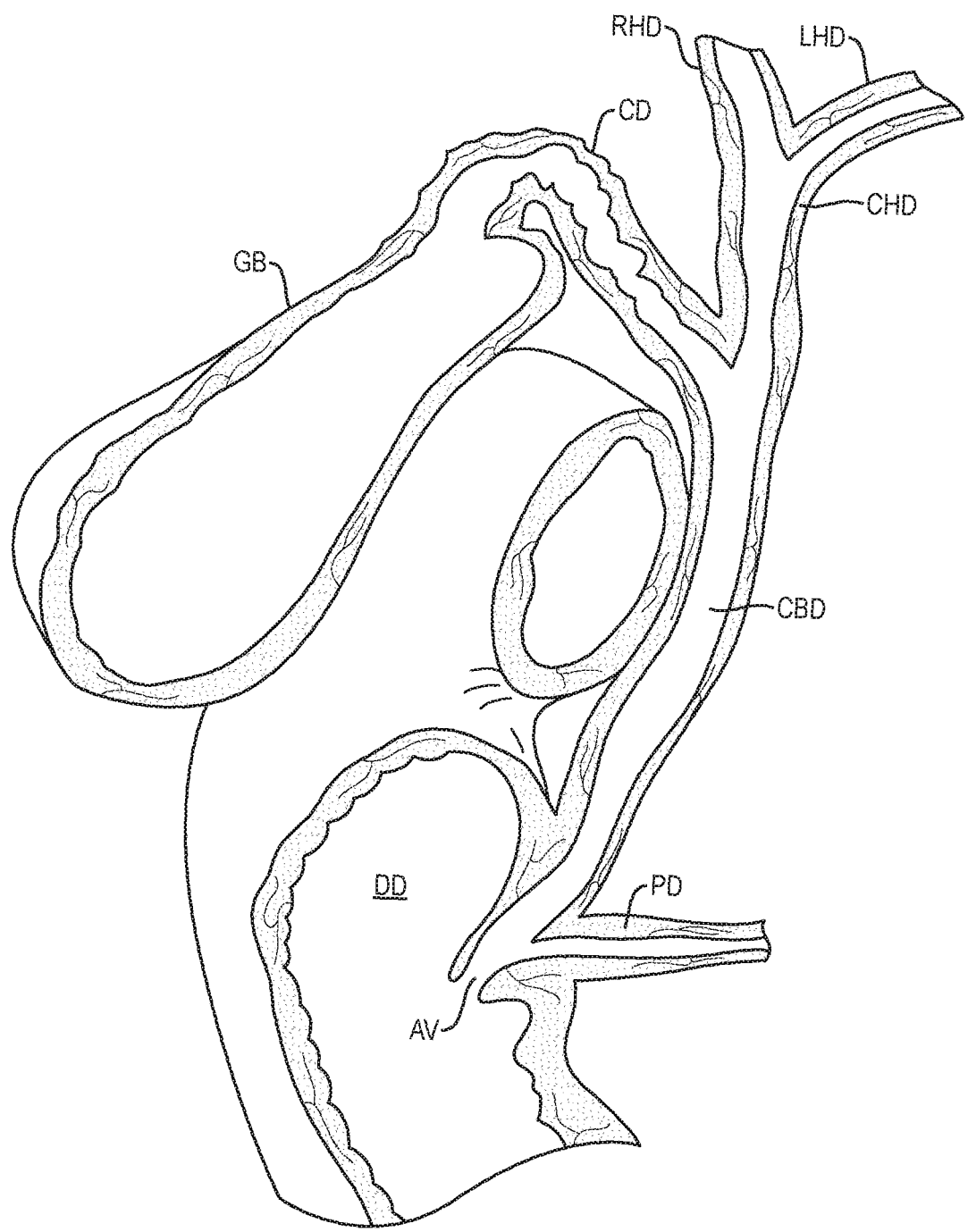
FIG. 1 illustrates portions of the biliary and pancreatic duct systems.

Referring to FIG. 1, the biliary system of a typical patient is shown. Bile, required for the digestion of food, is excreted by the liver into passages that carry the bile into the left hepatic duct LHD and the right hepatic duct RHD. These two hepatic ducts merge to form the common hepatic duct CHD as shown. The common hepatic duct CHD exits the liver and joins the cystic duct CD from the gallbladder GB, which stores bile, to form the common bile duct CBD. The common bile duct, in turn, joins with the pancreatic duct PD from the pancreas to feed bile, pancreatic juice and insulin into the descending part of the duodenum DD through the ampulla of Vater AV. A sphincter, known as the sphincter of Oddi (not shown), is located at the opening of the ampulla of Vater AV into the duodenum DD to prevent matter in the duodenum from traveling in a retrograde direction up into the common bile duct CBD. While the present invention will be described with particular reference to stents located in the lower common bile duct CBD and extending into the descending duodenum DD, the principles apply to a variety of other luminal structures as well.

Tumor growth, hyperplasia, pancreatitis or other strictures in or around the biliary duct tree outlined above can impede or block the flow of fluid from the liver, gallbladder and/or pancreas to the duodenum. To alleviate the effects of the stricture, a stent may need to be placed in a portion of the biliary system. The stent may be placed endoscopically. One procedure for placing the stent is endoscopic retrograde cholangiopancreatography (ERCP). ERCP is a technique that combines the use of endoscopy and fluoroscopy to diagnose and treat certain problems of the biliary or pancreatic ductal systems. The procedure involves placing an endoscope down the esophagus, through the stomach, into the duodenum, then passing various accessories through the endoscope instrumentation channel up through the ampulla of Vater into the biliary or pancreatic ductal systems. Alternatively, a special slim-diameter endoscope, sometimes referred to as a peroral cholangioscope, may be passed directly into the bile or pancreatic ducts. Stents currently placed by ERCP are straight tubes that generally have a constant diameter in their expanded state, and exhibit a number of drawbacks that are overcome by the present disclosure, as will be subsequently described. The stents disclosed herein overcome a number of limitations of the straight tubes used in ERCP procedures.

In some embodiments the stents described herein are deployed with an endoscope having ultrasound guidance. Current ultrasound endoscopes have one open lumen to pass a tool through. These ultrasound endoscopes do not have additional lumens to utilize additional tools. These endoscopes with ultrasound ability have ultrasound guidance that can be used to locate a target region of a body lumen outside of the endoscope or body lumen with the endoscope. A procedure using ultrasound guidance can be referred to as a EUS (endoscopic ultrasound) procedure.

In some embodiments the stents disclosed herein are deployed using a catheter or other delivery device. Examples of catheter devices that can be used to deliver the devices disclosed herein include the devices disclosed in application Ser. No. 13/871,978 filed on Apr. 26, 2013 that published as US 2013/0310833 and application Ser. No. 14/186,994 filed on Feb. 21, 2014, each of which are incorporated by reference in their entirety.

A variety of examples of stent configurations and shapes are illustrated in FIGS. 2A, 2B, 3, 4, 5A-5B, 6A-6B, 7A-7B, 8A-8B, 9A-9B, 10A-10B, 13A-13G, 14A-14J, 15A-15C, and 16A-16D that can be used with the methods and devices disclosed herein. The tissue anchor or stent can be made out of a shape memory alloy such as Nitinol. The stents can be self-expanding such that the stent expands from a constrained tubular position to the expanded configurations illustrated in FIGS. 2B, 3, 4, 5A-5B, 6A-6B, 7A-7B, 8A-8B, 9A-9B, 10A-10B, 13A-13G, 14A-14J, 15A-15C, and 16A-16D.

Figure 2A:
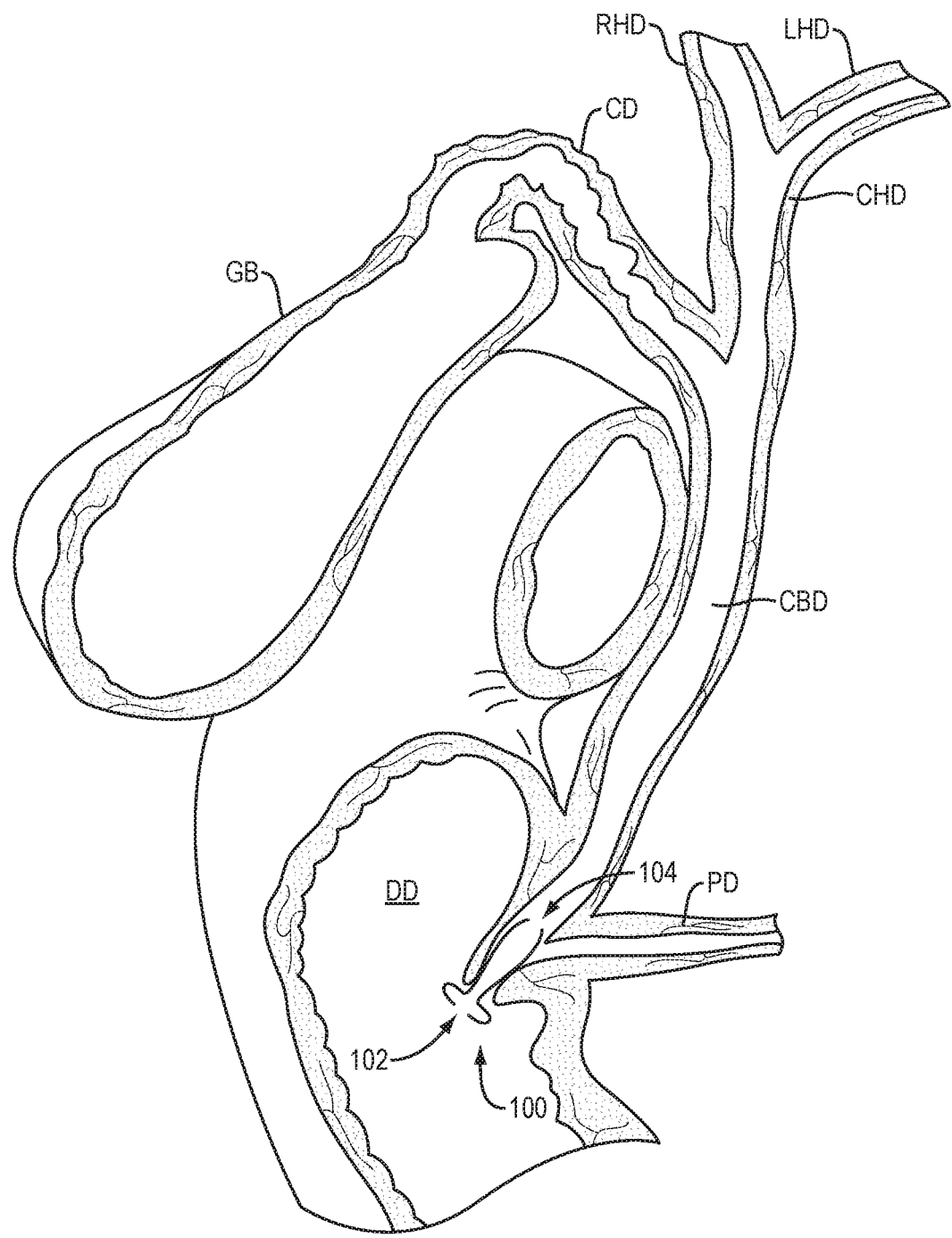
FIG. 2A illustrates an exemplary stent constructed according to aspects of the present disclosure and implanted in the common bile duct CBD.

Referring to FIG. 2A, an exemplary biliary stent 100 constructed according to aspects of the present disclosure is shown implanted in the lower end of the common bile duct CBD. In such a configuration, stent 100 may be used to treat an ampullary stenosis. In other embodiments, the stent may be longer to bridge a bile duct stricture higher upstream. Stent 100 comprises a downstream end 102 that protrudes into the duodenum DD, and an upstream end 104 that extends up into the common bile duct CBD. Stent 100 is shown in a generally radially expanded and axially foreshortened state, such that it is contacting the walls of the common bile duct CBD continuously along its length, or at least in several places. Stent 100 may be delivered endoscopically, such as with instrumentation similar to that described in co-pending application Ser. No. 13/363,297, filed Jan. 31, 2012. During delivery, stent 100 may be placed in an elongated tubular configuration within a delivery sheath. Once it is determined that stent 100 is properly positioned in a desired lumen location, the sheath may be retracted to expose stent 100 and allow it to expand from the elongated tubular configuration to the radially expanded configuration.

Figure 2B:
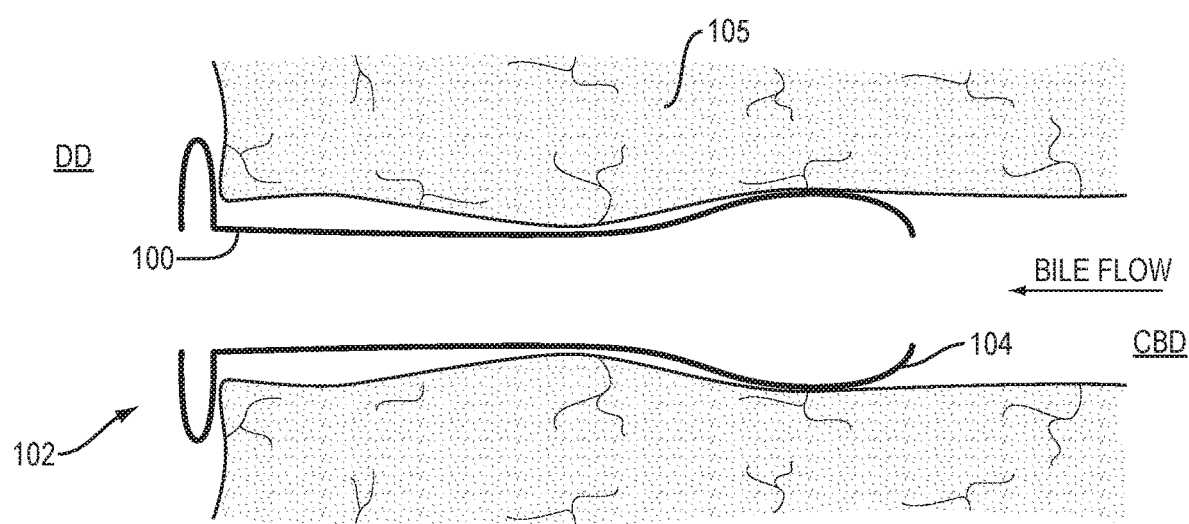
FIG. 2B is an enlarged view of the exemplary stent shown in FIG. 2A implanted in the common bile duct CBD.

Referring to FIG. 2B, an enlarged view of biliary stent 100 is depicted crossing a stricture 105 in a common bile duct CBD.

Figures 3, 4:
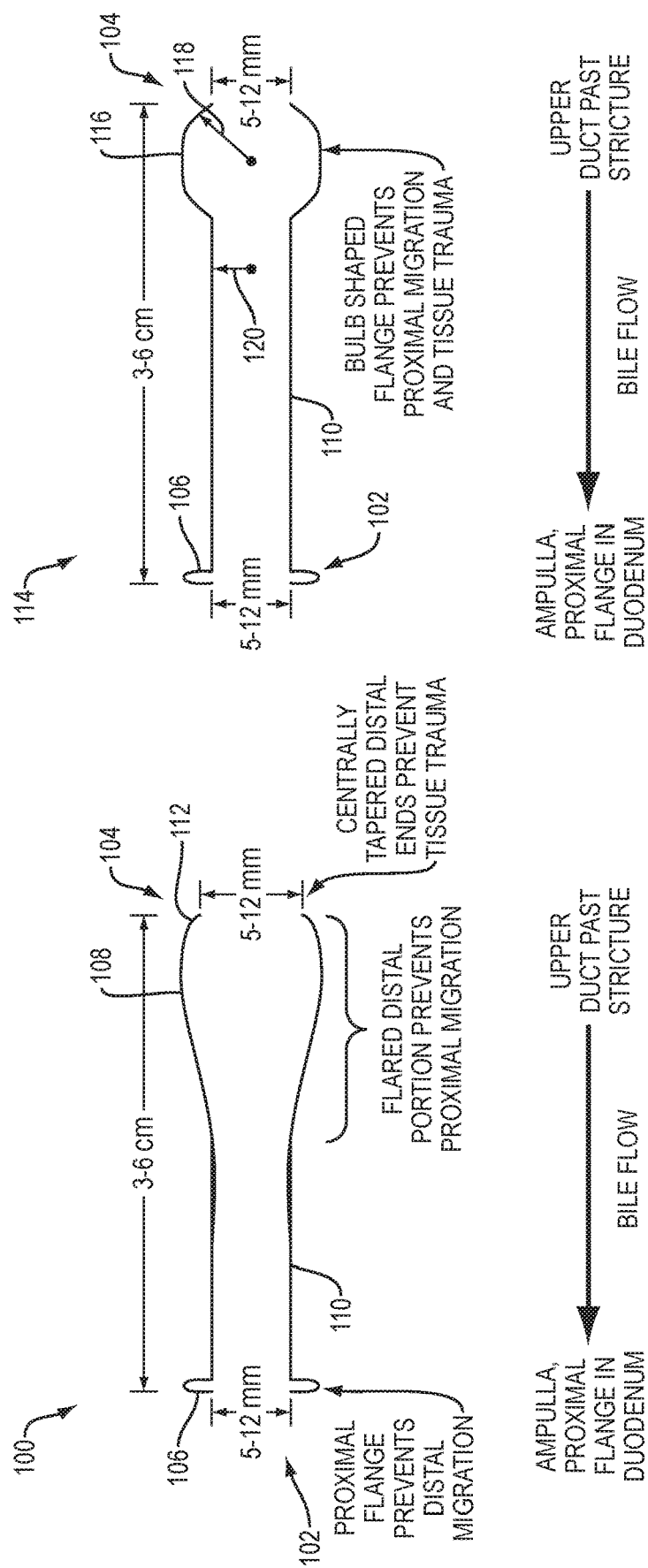
FIG. 3 is an enlarged lateral view of the exemplary stent shown in FIGS. 2A and 2B.
FIG. 4 is an enlarged lateral view of another exemplary stent.

Referring to FIG. 3, biliary stent 100 is shown in its radially expanded configuration. A double-walled downstream flange 106 may be formed at the downstream end 102 as shown. Downstream flange 106 is configured to prevent upstream migration of stent 100, such as by abutting against the wall of the duodenum DD (as shown in FIG. 2). A flared upstream portion or flange 108 may be formed at the upstream end of stent 100 as shown. A central saddle region 110 is provided between downstream flange 106 and upstream flange 108. In this embodiment, the saddle region has a generally constant diameter that is smaller than a maximum diameter of both the downstream flange 106 and the upstream flange 108. Upstream flange 108 is configured to prevent or inhibit downstream migration of stent 100. When moving upstream along the common bile duct CBD from the ampulla of Vater AV, the diameter of the common bile duct CBD tends to get larger. Additionally, a stricture or other deformity in the duct that stent 100 is intended to cross will tend to have a reduced diameter compared with adjacent portions of the duct. In some embodiments, the upstream and radially outward extending configuration of upstream flange 108 engages with the narrowing portion of the duct to prevent or inhibit downstream migration of stent 100.

Conventional straight stents having a generally constant diameter when radially expanded do not have the above anti-migration features. To address migration issues, conventional stents often incorporate undesirable features. For example, the stent may be designed to be much longer than the stricture it is intended to cross, because, due to possible migration, it is not certain where the stent will end up. Since a stent typically foreshortens as it expands radially, its final length will depend on the extent to which it expands inside a stricture. Adding extra length to compensate for this uncertainty can cause undesirable effects, such as the downstream end sticking way out into the duodenum DD. With this configuration, food traveling through the duodenum may catch on the stent, thereby bending, clogging and/or further moving the stent. The downstream end of the stent may even contact the duodenum wall opposite the opening to the common bile duct CBD, which may also inhibit or prevent fluid flow through the stent and/or cause tissue injury or perforation. Conventional stents that extend and/or migrate too far upstream in the common bile duct CBD may block one or more duct branches, such as the, cystic duct CD, left hepatic duct LHD, and/or right hepatic duct RHD. Stents constructed according to the present disclosure may be as short as 3 cm or shorter, and may be placed more precisely such that they will not block fluid flow through duct branches. In some embodiments, stent 100 has a length between about 3 cm and about 6 cm.

Conventional stents may also be uncovered or include features that allow tissue ingrowth to prevent the stent from migrating. This arrangement often leads to the undesirable effect of tissue in-growth through the stent causing a blockage that restricts or completely blocks the flow through the stent. Tubular stents also have upstream and downstream ends that are sharp due to wire termination, a situation that can cause irritation and undesirable hyperplastic tissue growth that can block the upstream end and restrict bile flow. Additionally, removal of the stent may become difficult, cause excessive trauma, or may be impossible without causing unacceptable trauma to the duct, again due to excessive tissue growth. These adverse effects may be avoided by the stent configurations described herein.

The gentle curves of flared upstream flange 108 shown in FIG. 3 are designed to hold stent 100 in place without causing undue irritation or trauma to the bile duct walls. It is believed that sharper features, such as tight radii, abrupt openings or abrupt stent ends can irritate the normal tissue of the lumen walls. Such irritation can cause hyperplasia (abnormally rapid tissue growth in the lumen wall to counteract the irritation). This tissue growth around the stent can cause the stent to be crushed inward, thereby restricting or blocking fluid flow. If the hyperplasia is near the end of the stent, the tissue can grow in front of and/or into the end of the stent, creating a new stricture and also restricting or blocking fluid flow. The applicants have found that by configuring upstream flange 108 with a large radius, and by placing at least a slight inward curl 112 at the upstream opening of stent 100 as shown, or other feature with a reduced diameter, such that the upstream end of the tubing does not contact and chafe the adjacent tissue, undesirable hyperplasia may be avoided. Since tumorous tissue does not tend to exhibit hyperplasia, reducing the length of the stent to be about the same length as that of the stricture can be advantageous. According to aspects of the present disclosure, the stent may be configured so that it adjusts to the length of the stricture.

In some embodiments, the inner diameter of the upstream and downstream openings and of the saddle region is between about 5 mm and about 12 mm, while the maximum outer diameter of the upstream flange is between about 20 mm and about 30 mm (in the deployed, radially expanded configuration). In some embodiments, the upstream flange 108 has an axial length that is at least as long as the axial length of saddle region 110. In some embodiments, the upstream flange 108 has an axial length that is at least one-fourth as long as the axial length of saddle region 110.

Referring now to FIG. 4, another exemplary embodiment is shown. Stent 114 is constructed with features similar to those of stent 100 shown in FIG. 3. A bulb-shaped upstream flange 116 is provided to prevent or inhibit tissue trauma and downstream migration of stent 114. In some embodiments, upstream flange 116 comprises an axial radius 118 that is at least double a lateral radius 120 when stent 114 is in the foreshortened, deployed configuration, as shown. As with the previous embodiment, the upstream intraductal flange is designed to anchor in the lumen above the stricture while minimizing tissue trauma. The knob-like 'shouldered' configuration 116 distributes pressure along a larger rounded surface area. The end of the stent is not sharp and does not dig into the tissue wall. Upstream flange 116 may be kept short to minimize contact with the normal upstream bile duct and minimize the risk of obstructing drainage of feeding tributary ducts, such as the cystic duct and the bifurcation of the hepatic duct, for example. In some embodiments the upstream flange does not fully expand inside the duct, but instead maintains a radially outward force on the duct to reduce migration.

Stents constructed according to the present disclosure can be used to cross strictures virtually anywhere in the biliary and pancreatic systems. In some embodiments, the downstream end flange of the stent is always located in the duodenum and the stent length is tailored to the location of the stricture. For example, a relatively short stent may be used to cross a stricture located in or near the ampulla of Vater. A longer stent may be used to cross a stricture located between the cystic duct and the bifurcation between the left and right hepatic ducts. In yet another embodiment, the stent can have upstream and downstream ends constructed similarly to the upstream flange 116 of FIG. 4 allowing the entire stent to be placed within the duct, bridging the stricture without extending into the duodenum. According to aspects of the present disclosure, the stent may be removable. In some embodiments the stents described herein can include a loop on either or both ends of the stent. The loop can facilitate retrieval of the stent using a snare or other retrieval technique. For example, a wire or filament loop may be utilized to snare the downstream flange in the duodenum such that the entire stent may be pulled out of the duct and removed through the duodenum. In another example a loop can be utilized on the upstream flange in the bile duct or stomach such that the upstream flange is pulled inside out of the duct and removed from the body.

Stents constructed according to the present disclosure can also be used to connect other lumens, such as connecting a hepatic duct or parenchyma in the liver with the stomach, or a pancreatic duct with the stomach, or the common bile duct with the stomach or duodenum to drain fluid from the ducts if blocked further downstream.

The stents disclosed herein also provide benefits over conventional rigid rivet type anastomotic devices used in the GI tract because the stents firmly and atraumatically engage the tissue walls and do not form necrotic tissue. In some embodiments the stents disclosed herein can be configured to be retrievable and removable after implantation. In some embodiments the stents can be designed for chronic or permanent implantation.

In some embodiments, stent 100 of FIG. 3 and stent 114 of FIG. 4 comprise a body formed from a woven filament braid. The filament will typically be a metal wire, more typically being a nickel-titanium or other super-elastic or shape memory metal wire. Alternatively, in cases where elasticity is less critical, a filament could be formed from a polymeric material, such as polypropylene, polyethylene, polyester, nylon, PTFE, or the like. In some cases, a bio-absorbable or bio-degradable material, typically a biodegradable polymer, such as poly-L-lactic acid (PLLA), could find use.

The body may have both an elongated tubular configuration (for delivery of the stent) and a foreshortened configuration (when deployed) where downstream and upstream ends of the body expand radially (as the body is foreshortened). One or both of the ends may expand into double-walled flange structures. Such "double-walled flange structures" may be formed as a portion of the body, typically an end-most portion but optionally some portion spaced inwardly from the end, moves inwardly (toward the middle) so that a pair of adjacent body segments within the portion are drawn together at their bases so that a midline or a crest line bends and expands radially to form a pair of adjacent annular rings which define the double-walled flange structure. See downstream flange 106 in FIGS. 3 and 4, for example. After such foreshortening and deployment of the double-walled flange structures, the body may further have a cylindrical saddle region between the flange structures.

When formed from shaped memory metal wires, such as nitinol or eligiloy, the wires may have a relatively small diameter, typically in the range from 0.001 inch to 0.02 inch, usually from 0.002 inch to 0.01 inch, where the braid may include from as few as 10 to as many as 200 wires, more commonly being from 20 wires to 100 wires. In exemplary cases, the wires will be round having diameters in the range from 0.003 into the 0.007 inch with a total of from 24 to 60 wires. The wires may be braided into a tubular geometry by conventional techniques, and the tubular geometry may be heat-treated to impart the desired shape memory. Usually, the braided tube will be formed into the desired final (deployed) configuration with the flanges at each end. Such a flanged configuration may then be heat set or formed into the braid so that, in the absence of a radially constraining or axially elongating force, the stent will assume the foreshortened configuration with the flanges at each end. Such foreshortened-memory configurations allow the stent to be delivered in a constrained configuration (either radially or axially elongated) and thereafter released from constraint so that the body assumes the flanged configuration at the target site.

In alternative embodiments, however, the woven filament braid may be heat set into the elongated tubular configuration and shifted into the foreshortened, flanged configuration by applying an axial compressive force. Such axial compression will foreshorten and radially expand the flanges and allow a controlled and adjustable foreshortening, allowing the stent to be adjusted to a desired length. The woven filament braid, according to this embodiment, can be heat set to the expanded configuration and include a means to mechanically foreshorten the stent beyond its normal fully expanded configuration, allowing the stent to automatically or manually adjust to the length of the stricture. The foreshortening and flanges may be formed by providing sleeves, tubes, rods, filaments, tethers, springs, elastic members or the like, which apply spontaneous or applied force to the tube to create foreshortening and flange formation. Optionally or additionally, the body may have weakened regions, reinforced regions, or be otherwise modified so that the desired flange geometries are formed when a force is applied to cause axial foreshortening.

The stents may be adapted to be delivered by a delivery device, typically an endoscopic delivery catheter, usually having a small diameter in the range from 1 mm to 8 mm, usually from 2 mm to 5 mm. Thus, the elongated tubular configuration of the stent body will usually have a diameter less than that of the catheter diameter, usually from 0.8 mm to 7.5 mm, more usually from 0.8 mm to 4.5 mm, where the flange structures will be expandable significantly, usually being in the range from 3 mm to 70 mm, more usually in the range from 5 mm to 40 mm. A variety of stents having different lengths may be provided, in kit form for example, for use on strictures in different locations. In some embodiments, the overall lengths of the stents in their fully expanded/deployed state are 7, 9 and 11 cm. In other embodiments the lengths are 6, 8 and 10 cm. In yet other embodiments, the stents will have lengths between 1 and 6 cm. The cylindrical saddle region of the stent will often not increase in diameter during deployment, but may optionally increase to a diameter from 2 mm to 50 mm, more usually from 5 mm to 12 mm. When present, the lumen or passage through the deployed stent can have a variety of diameters, typically from as small as 0.2 mm to as large as 40 mm, more usually being in the range from 1 mm to 20 mm, and typically having a diameter which is slightly smaller than the expanded outside diameter of the cylindrical saddle region. The length of the body may also vary significantly. Typically, when in the elongated tubular configuration, the body will have a length in the range from 7 mm to 100 mm, usually from 12 mm to 70 mm. When deployed, the body may be foreshortened, typically by at least 20%, more typically by at least 40% and often by 70% or greater. Thus, the foreshortened length will typically be in the range from 2 mm to 80 mm, usually in the range from 30 mm to 60 mm.

The body of the stent may consist of the woven filament braid with no other coverings or layers. In other instances, however, the stent may further comprise a membrane or other covering formed over at least a portion of the body. Often, the membrane is intended to prevent or inhibit tissue ingrowth to allow the device to be removed after having been implanted for weeks, months, or longer. Suitable membrane materials include polytetrafluoroethylene (PTFE), expanded PTFE (ePTFE), silicone, polypropylene, urethane polyether block amides (PEBA), polyethylene-terephthalate (PET), polyethylene, C-Flex® thermoplastic elastomer, Krator® SEBS and SBS polymers, and the like.

Such membranes may be formed over the entire portion of the stent body or only a portion thereof, may be formed over the exterior or interior of the body, and will typically be elastomeric so that the membrane conforms to the body in both the elongated and foreshortened configurations. Optionally, the membrane may be formed over only the central saddle region, in which case it would not have to be elastomeric when the central saddle region does not radially expand.

The covering or membrane inhibits tissue ingrowth within the interstices of the wire mesh and minimizes fluid leakage when the stent is implanted. Reducing tissue ingrowth improves the removability of the stents. In contrast to vascular stents, which are typically not designed to be moved or retrieved, the stents illustrated herein are collapsible and designed to be removable and retrievable. The stents also typically do not include barbs or other sharp projections used in some other types of stents to permanently secure the stent to surrounding tissue.

Different parts of the stent can be covered or uncovered depending on the specific application. In some embodiments one end of the stent can have an uncovered portion. In some embodiments any of the stents disclosed herein can include a covering on one of the ends of the stent. The covering can be on a flanged end of the stent or an end of the stent without a flange. For example, if deploying one end of the stent in the liver and the other end in the stomach then the end of the stent within the liver could be uncovered with the cylindrical saddle region and end interfacing the stomach covered. If deploying one end adjacent to the ampulla of Vater and duodenum and the other end in the bile duct than the bile duct end would be covered. In some embodiments any of the stents disclosed herein can include a covering on both of the ends of the stent. In some embodiments a middle portion or portion between the upstream and downstream flanges can be uncovered. An uncovered middle portion can be used to drain fluid from the pancreatic duct when the ends of the stent are placed in the duodenum and bile duct.

In some embodiments the cylindrical saddle region is covered to prevent fluid from leaking outside of the cylindrical saddle region of the stent. The stents disclosed herein can be deployed within the body such that the cylindrical region forms a fluid conduit between the body lumens in the peritoneum as described herein. The covered cylindrical saddle region can prevent leakage into the peritoneum. Leaking biological material into the peritoneum can cause serious complications, as a result the stents can have a covering to prevent fluid or material leaking outside of the cylindrical saddle region of the stent. Coverings can also be used on the end of the stent that is configured to connect to the stomach or duodenum.

Examples of manufacturing techniques that can be used to produce the stents disclosed herein include using laser cutting, weaving, welding, etching, and wire forming. A membrane material such as silicon can be applied to the wire stent frame to prevent the passage of fluid through the stent walls. The membrane or covering material can be applied by painting, brushing, spraying, dipping, or molding.

The strength of the double-walled flanged structure(s) will depend on the number, size, stiffness, and weave pattern(s) of the individual wires used to form the tubular stent body. For example, a design with a large number of nitinol wires, for example 48, but a relatively small wire diameter, for example 0.006 inches, will form a braid structure with a saddle region which remains flexible and double-walled flange(s) which is/are relatively firm. Use of fewer wires, for example 16, and a larger wire diameter, for example 0.016 inches, will form a braid structure with a relatively rigid saddle region and relatively stiff, non-flexible flange(s). Both rigid and flexible designs can be desirable, depending on the application. In particular, in some embodiments the double-walled flange structure(s) has/have a preselected bending stiffness in the range from 1 g/mm to 100 g/mm, or in the range from 4 g/mm to 40 g/mm. Similarly, in some embodiments, the central saddle region has a preselected bending stiffness in the range from 1 g/mm to 100 g/mm, or from 10 g/mm to 100 g/mm.

The bending stiffness of the flange can be determined by the following test. The distal flange is secured in a fixture. The outer diameter of the flange is pulled in a direction parallel to the axis of the stent using a hook attached to a Chatillon force gage. The saddle of the stent is held in a hole in a fixture and force (grams) and deflection (mm) are measured and recorded. The bending stiffness of the flange can be determined by the following test. The distal flange is secured in a fixture. The outer diameter of the flange is pulled in a direction perpendicular to axis of the stent using a hook attached to a Chatillon force gage. The saddle of stent is held in a hole in a fixture and force (grams) and deflection (mm) are measured and recorded.

The shape and design of the stent can be selected based on the desired application. For example, embodiments of stents and methods disclosed herein include forming a direct fluid conduit between body lumens that are not typically connected (e.g. stomach to gallbladder, etc.). In these embodiments the ends or flanges of the stents can be selected to provide for sufficient strength and flexibility to hold the tissue planes. In some embodiments the stents and methods disclosed herein can be used to improve flow in natural pathways within the body. In these embodiments the shape and design of the stent can be selected based on the desired properties for these applications.

The stent designs also offer improved lateral strength and pullout force over conventional stents. The pullout force can be determined using two different tests, a stent pull-out force test and an implant anchor pull-out test.

For the pull-out force test the stent is tested in a fully expanded configuration. The stent is deployed through a hole in a material sized to accommodate the expanded diameter of the cylindrical saddle region of the stent. For example, the hole in the material can be around 10 mm or 15 mm depending on the stent size. The stent pull-out test measures the force required to deform the distal flange of the fully expanded stent and to pull the expanded distal flange of the stent through the opening. The stent is pulled proximally using a fastener attached to a force gauge. Proximal force is applied until the distal flange is dislodged from the material and the force of dislodgement is measured and recorded as the "pull-out force", measured in grams, and deflection, measured in mm, is measured and recorded. In some embodiments the stent pull-out force is greater than about 260 grams (about 2.55 N). In some embodiments the stent pull-out force is greater than about 300 grams (about 2.94 N). In some embodiments the stent pull-out force is greater than about 400 grams (about 3.92 N). In some embodiments the stent pull-out force is greater than about 500 grams (about 4.9 N). In some embodiments the stent pull-out force is greater than about 550 grams (about 5.39 N). In some embodiments the stent pull-out force is greater than about 600 grams (about 5.88 N). In some embodiments the stent pull-out force is greater than about 700 grams (about 6.86 N). In some embodiments the stent pull-out force is greater than about 800 grams (about 7.84 N). In some embodiments the stent pull-out force is greater than about 900 grams (about 8.82 N). In some embodiments the stent pull-out force is greater than about 1000 grams (about 9.8 N).

For the implant anchor test the strength of the distal flange is tested while the proximal flange of the stent is held by the catheter device in a constrained position. The distal flange is deployed on the other side of a rigid material having a hole sized to accommodate the shaft of the catheter. The catheter can be pulled with the force measured that is required to deform the distal flange and pull the distal flange through the hole in the rigid material. In some embodiments the stent has an implant anchor test strength of greater than about 1 N. In some embodiments the stent has an implant anchor test strength of greater than about 2 N. In some embodiments the stent has an implant anchor test strength of greater than about 3 N. In some embodiments the stent has an implant anchor test strength of greater than about 4 N. In some embodiments the stent has an implant anchor test strength of greater than about 5 N. In some embodiments the stent has an implant anchor test strength of greater than about 6 N. In some embodiments the stent has an implant anchor test strength of greater than about 7 N. In some embodiments the stent has an implant anchor test strength of greater than about 8 N. In some embodiments the stent has an implant anchor test strength of greater than about 9 N. In some embodiments the stent has an implant anchor test strength of greater than about 10 N. In some embodiments the stent has an implant anchor test strength of greater than about 15 N.

The stent shapes can vary. FIGS. 2A, 2B, 3, 4, 5A-5B, 6A-6B, 7A-7B, 8A-8B, 9A-9B, 10A-10B, 13A-13G, 14A-14J, 15A-15C, and 16A-16D illustrate a variety of stent shapes and cross-sections. For example, the end or flange shape can be optimized to improve the strength of the stent and to provide a sufficient amount of linear force opposing each tissue plane while allowing smooth fluid and material flow through the inner opening of the composite structure. In some embodiments end shapes can be described as "bell-like", consisting of multiple structural folds, having a plurality of inflection points, etc. The inflection point can be considered a point of a curve at which a change in the direction of curvature occurs. Additional ends might be rolled or may protrude retrograde against the tissue plane. Alternate designs might consist of a mouth that is wider than the inner diameter of the device.

In some embodiments the stent ends are symmetrical. In some embodiments the stent ends can have different end shapes. The stent end shapes can be selected based on the body lumens and location where the stent is deployed and the desired physical properties. The stents can be designed to facilitate unidirectional flow of fluid and material. The unidirectional flow can also exert or require additional strength for the leading stent flange (e.g. upstream flange) that first contacts the flow of material. The upstream flange can be designed with a cross-section that has a stronger pull-out force than the downstream flange. The diameter of the opening in the upstream flange can have a wider design than the downstream flange to minimize the chances of fluid or material getting stuck within the flange. The end of the upstream flange can also be designed to further decrease the chances of getting fluid or material stuck in the flange. For example a stent could have the cross-section illustrated in FIG. 14A for the upstream flange with its wider flange end and a flange design like FIG. 14I for the downstream flange as illustrated in FIG. 14J.

Any of the stents disclosed herein can include a windsock type structure. The windsock structure can facilitate one-way fluid flow from the interior of the stent through the windsock while preventing or minimizing the flow of material through the windsock and into the interior of the stent. The windsock can be coupled to the downstream end of the stent. The windsock can have a length suited to the particular application and desired fluid flow pathway. For example, the windsock can have a length sized to run from an area of the duodenum to the jejunum. In some embodiments the stent is configured such that an upstream end is sized for deployment in the bile duct or pancreatic duct and a downstream end is configured to be within the duodenum adjacent to the Ampulla of Vater with the windsock coupled to the downstream end and running from the duodenum to the jejunum. In this embodiment digestive juices would flow from the upstream end of the stent in the pancreatic duct or bile duct through the stent and windsock to the jejunum thereby by passing the duodenum. The windsock can also have a length sized to run from an area of the stomach to the jejunum. In some embodiments the stent is configured such that an upstream end is sized for deployment in the bile duct, pancreatic duct, or liver and a downstream end is configured to be within the stomach with the windsock coupled to the downstream end and running from the stomach to the jejunum. In this embodiment digestive juices would flow from the upstream end of the stent in the pancreatic duct, bile duct, or liver through the stent and windsock to the jejunum thereby by passing the stomach and duodenum. These example applications can provide benefits associated with gastric bypass procedures (Roux-en-Y) without requiring invasive surgeries used in gastric bypass procedures.

The dimensions of the stent can be designed to provide a desired hold on the tissue walls along with a desired conduit for fluid flow. For example, the width and diameter of the flange can be optimized to provide the desired properties. A cuff or lip can be provided distally to the flange to provide additional strength. The diameter and length of the cuff can also be optimized to modify the properties of the stent. The diameter of the cuff can be greater than the diameter of the cylindrical hollow portion. This can make subsequent access to the stent easier and decrease the chance of material getting stuck in the flange. The cuff or outer lip can also be shaped to minimize the chance of fluid or material getting stuck within the flange volume. For example, the outer cuff or lip can include a wall that projects or curls away from the interior volume of the stent. The diameter and length of the cylindrical portion can be optimized based on the thickness of the tissue walls and desired stent location. The overall length of the stent can also be optimized based on the specific application.

In some embodiments any of the flange cross-sections disclosed herein can be used with any of the other stent flanges or cross-sections disclosed herein. For example, the flange 106 illustrated in FIGS. 8A-8B can be replaced with any of the flanges illustrated in FIGS. 13A-153, 14A-14J, 15A-15C, and 16A-16D such that the stent has the flange of FIGS. 13A-13G, 14A-14J, 15A-15C, and 16A-16D and the cylindrical portion 156 on the other end. In another example the flange 164, 164A of FIGS. 10A-10B could be replaced by any of the flanges illustrated in FIGS. 13A-13G, 14A-14J, 15A-15C, and 16A-16D.

While in some embodiments the self-expanding stent bodies are formed from shape memory alloys, other designs could employ elastic tethers which join the ends of the body together. Thus, the bodies could have a low elasticity, where the force for axially compressing the ends comes from the elastic tethers. Such designs may be particularly suitable when polymeric or other less elastic materials are being used for the body of the stent.

In still other embodiments, the stents may comprise a lock which maintains the body in a foreshortened configuration. For example, the lock may comprise a rod or a cylinder within the body which latches to both ends of the body when the body is foreshortened. Alternatively, the lock could comprise one, two, or more axial members which clamp over the lumen of the stent body when the body is foreshortened.

As a still further option, the stent could comprise a sleeve formed over a portion of the cylindrical saddle region. The sleeve will both maintain the diameter of the central saddle region and will limit the inward extension of the flanges, help forming the flanges as the stent body is axially foreshortened.

Referring to FIGS. 5A-10B, additional stent embodiments are shown, employing similar features to those previously described.

FIG. 5A shows another exemplary stent 130 having an upstream flange 132 that is generally cylindrical in shape and having rounded portions at the proximal and distal ends of the upstream flange 132.

The stents disclosed herein can include covered and uncovered portions. FIG. 5B shows a stent 130' similar to FIG. 5A but with a portion of saddle region 110' uncovered. Leaving only a portion of the stent uncovered allows for a limited amount of tissue ingrowth to prevent migration of the stent, but may allow the stent to removable, at least for a limited amount of time. In another similar embodiment, the upstream and/or downstream ends of the stent are uncovered, allowing fluid flow from side branches of the ductal system, such as the cystic duct and the pancreatic ducts, to be unimpeded.

In some embodiments the covered portion of the stent can be as little as about 20% of the stent. For example, for a stent with one end configured to engage with the stomach and a second end configured to engage with another body lumen, as little as about 20% of the stent can be covered. The covered portion can be the portion of the stent configured to engage with the stomach, e.g. gastric end of the stent.

The uncovered portion of the stent allows fluid to flow into the internal area of the stent and to pass through to the other end of the stent. For example, the uncovered end of the stent can be placed in the liver. Pressure from bile in the liver can cause bile to flow through the uncovered portion of the stent and through the lumen in the stent and into another body lumen where the other end of the stent is secured, such as the stomach or duodenum. The portion of the stent engaging with the stomach or duodenum can be covered to minimize tissue ingrowth and improve the flow and delivery of fluid into the stomach. FIG. 6A shows another exemplary stent 136. The body 138 of the stent that is upstream of the downstream flange 106 has a gradually increasing diameter. FIG. 6B shows a similar stent 136' having a portion 140 of the body 138' that is uncovered, similar to the stent shown in FIG. 5B.

FIG. 7A shows another exemplary stent 142. Stent 142 comprises a double-walled downstream flange 144 and a double walled upstream flange 146. The inwardly facing wall of upstream flange 146 is configured to be flatter than the outwardly facing wall. FIG. 7B shows a similar stent 142' having a portion 148 of its saddle region 110' uncovered.

FIG. 8A shows another exemplary stent 150. Stent 150 comprises an upstream flange 152 having a ramped portion 154 leading up to a cylindrical portion 156. FIG. 8B shows a similar stent 150' having ramped portion 154' uncovered. In some embodiments the stent 150' can be used to drain a portion of the liver or related duct system. The uncovered ramp portion 154' and cylindrical portion 156' can be implanted or deployed within the liver. The uncovered ramp portion 154' allows for bile flow from the duct system and other areas of the liver with the bile flowing to the other end of the stent, which can be deployed in a body lumen such as the stomach or duodenum. The stent 150' illustrated in FIG. 8b has the uncovered portion (illustrated as the uncovered ramp portion 154') that can be used to facilitate drainage. The stent 150' can be deployed between the bile duct and duodenum with the downstream flange 106 deployed in the duodenum and the cylindrical portion 156' deployed in the bile duct. The uncovered ramp portion 154' can permit the flow of material from the pancreatic duct through the interior of the stent, out the exit adjacent to the downstream flange 106, and into the duodenum.

FIG. 9A shows another exemplary stent 158. Stent 158 comprises a double-walled downstream flange 144 and an identical double walled upstream flange 144. FIG. 9B shows a similar stent 158' having downstream flange 144' and upstream flange 144' uncovered.

FIG. 10A shows another exemplary stent 160. Stent 160 comprises a small diameter, double-walled downstream flange 162 and a large diameter, double walled upstream flange 164. FIG. 10B shows a similar stent 160' having the upstream flange 164'uncovered.

Figures 13A, 13B, 13C:
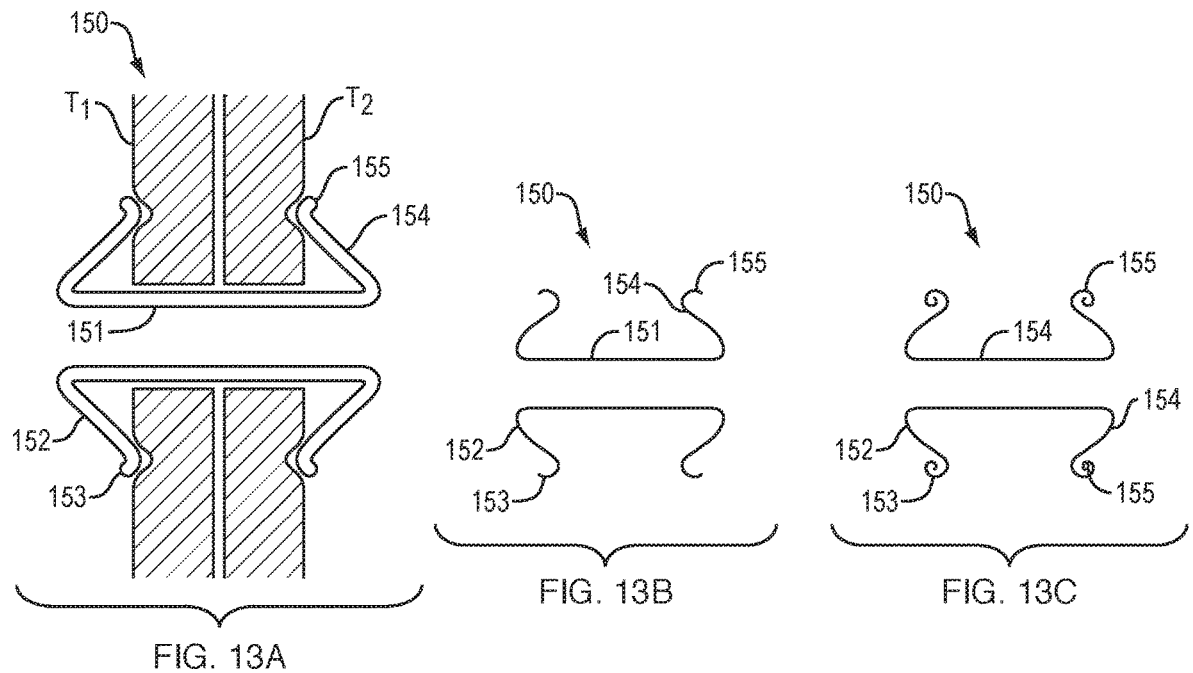
FIGS. 13A-13G illustrate cross sections of stents in accordance with some embodiments.

FIG. 13A illustrates a cross section of an embodiment of a stent 150 with a cylindrical saddle region 151, flange 152 with an end 153 configured to bend back towards flange 154, flange 154 with an end 155 configured to bend back towards flange 152. The flanges 152, 154 and ends 153, 155 are configured to hold the tissue walls T1, T2 in apposition. The distal portion of the flanges 152, 154 are curved to reduce trauma to the tissue walls. FIGS. 13B and 13C have a similar configuration to FIG. 13A but with the ends 153, 155 of the stent further curled. FIG. 13B shows the ends 153, 155 curled in roughly a half circle and FIG. 13C has ends 153, 155 forming approximately a full circle. The ends 153, 155 of the stents in FIGS. 13B-C can atraumatically engage the tissue with increased strength from the additional curling on the distal ends of the stent structure.

Figures 13D, 13E:
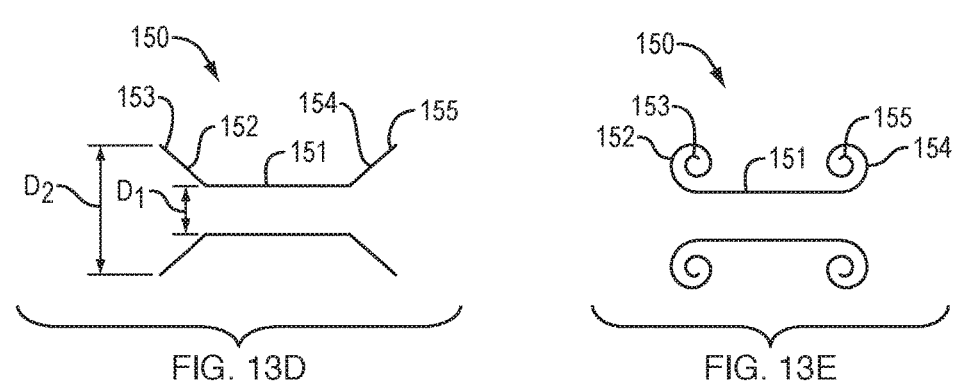
Figures 13F, 13G:
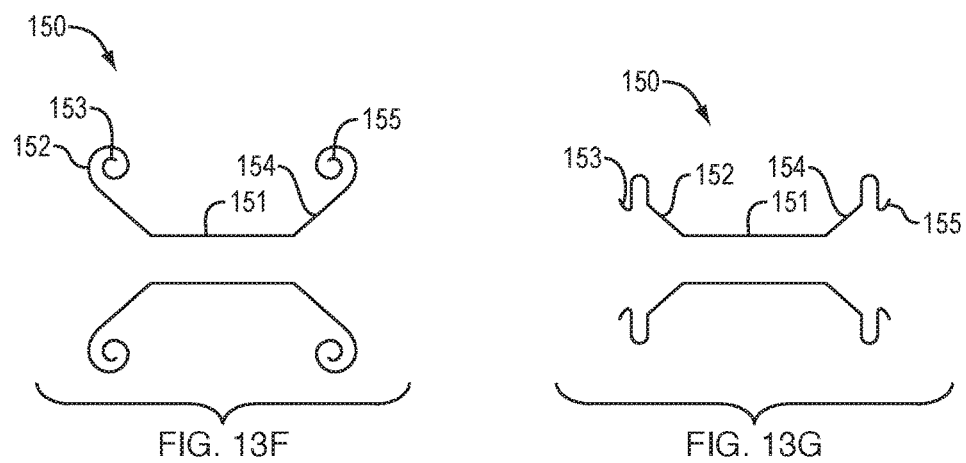

FIGS. 13D-13G illustrate additional cross-sectional views of stent structures. FIG. 13D illustrates a stent 150 with flange structures 152, 154 projecting away from the cylindrical saddle region 151. The cylindrical saddle region 151 has a diameter of D1 and the outer flange structure 152, 154 has a larger diameter D2. FIG. 13E illustrates a stent 150 with flange structures 152, 154 curling outward and away from the interior volume of the cylindrical saddle region 151. FIG. 13F illustrates flange structures 152, 154 that project away from the cylindrical saddle region 151 and have curled ends 153, 155. The curled end can provide additional lateral strength to the stent. FIG. 13G illustrates flange structures 152, 154 that project away from the interior volume of the cylindrical saddle region 151 and further include double walled flange structures to increase the strength of the stent 150 and to further engage atraumatically with the tissue walls when implanted.

FIGS. 14A-14J illustrate a variety of partial cross-sections for stent flange configurations. Some flange structures can have a volume within each flange that might trap fluid or other material passing through the stent. The flange can be designed to minimize the chance of fluid or other material getting trapped within the internal volume of the stent or stent flange. The stents illustrated in FIGS. 14A-14I have flange structures that are designed to minimize fluid and material getting trapped or stuck within the flange volumes.

FIG. 14A illustrates a partial cross section of a stent 160 with a flange structure 162 having a plurality of inflection points. The inflection points create radial bends in the three-dimensional stent structure. The flange 162 wall projects away from the cylindrical saddle region 161 (a first inflection point) then bending back towards the center of the longitudinal pathway 164 of the stent 160 (two more inflection points) followed by bending back again away from the center of the longitudinal pathway 164 of the stent 160 (two more inflection points) and an additional bend at the stent end 163 (one more inflection point). Each of the bends can be considered an inflection point. The stent 160 illustrated in FIG. 16A has 6 inflection points. The inflection points can add additional strength to the stent flange. The stent has an open end with a diameter that is greater than the diameter of the cylindrical saddle region 161 to reduce the likelihood of material getting stuck in the stent and to promote the flow of fluid through the stent body. The additional inflection point can increase the lateral strength and pullout force of the expanded stent.

FIG. 14B illustrates a stent 160 with a flange structure 162 having seven inflection points. The structure is similar to the stent illustrated in FIG. 14A but the outer stent wall angles back towards the center of the longitudinal pathway 164 at the end 163.

FIG. 14C illustrates a stent 160 with a flange structure 162 including a curled stent end 163. The curled end curls back towards the cylindrical saddle region 161 forming a circular cross-section. The end 163 of the stent flange bends back towards itself so that the fluid flow does not flow directly at the end of the stent. This stent configuration further decreases the likelihood fluid getting stuck within the internal volume of the flange 162.

FIG. 14D illustrates a stent 160 with a flange 162 projecting away from the longitudinal pathway 164 of the saddle region 161 and with an end 163 curling outwards past the outer point of the flange 162.

FIG. 14E illustrates a stent 160 with a flange 162 having five inflection points. The flange 162 projects outward away from the center of the saddle region 161 and then bends back towards the center pathway 164 followed by bending again with the end 163 projecting away from the longitudinal center 164 of the cylindrical saddle region 161.

FIG. 14F illustrates a stent 160 with a flange 162 projecting away from the cylindrical saddle region 161 and forming a curled circular cross-section with the end 163 curled back towards the flange 162.

FIG. 14G is similar to FIG. 14F but with the circular end 163 curling to form greater than a full circle at the end 163 of the stent.

FIG. 14H illustrates a stent flange 162 having multiple bends resembling right angles along with a curled end 163 curling away from the cylindrical center region 161. The right angles can increase the lateral strength and pullout force of the stent.

FIG. 14I illustrates a flange having a sinusoidal outer shape with a curled end curling away from the cylindrical saddle region. The wavy sinusoidal outer shape can increase the lateral strength and pullout force of the stent.

FIG. 14J illustrates a stent cross section one a flange having the structure illustrated in FIG. 14A and a flange illustrates in FIG. 14I. The flange illustrated in FIG. 14A has a wider opened and can be deployed such that it faces the direction of fluid flow. The flange illustrated in FIG. 14I has a narrower outer end and can be used as the opposing end where the material exits the internal volume of the stent.

Figure 15A:
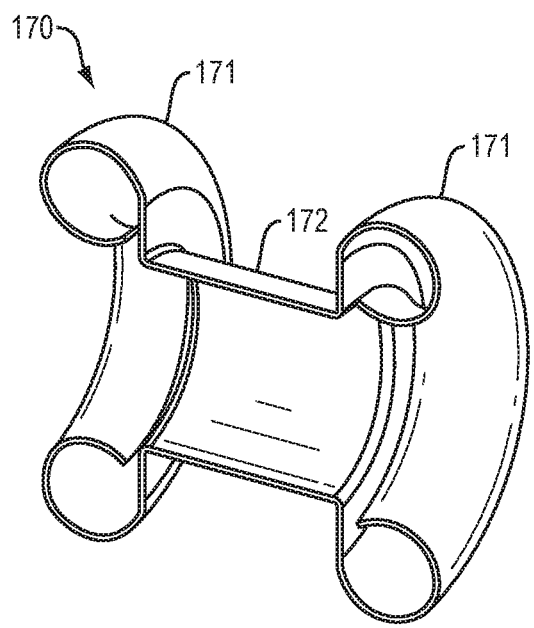
FIGS. 15A-15C illustrate stents in accordance with some embodiments.
Figure 15B:
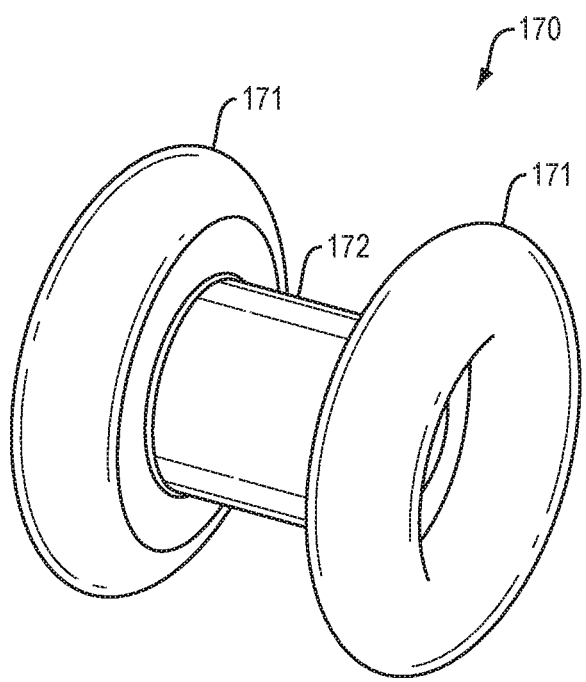
Figure 15C:
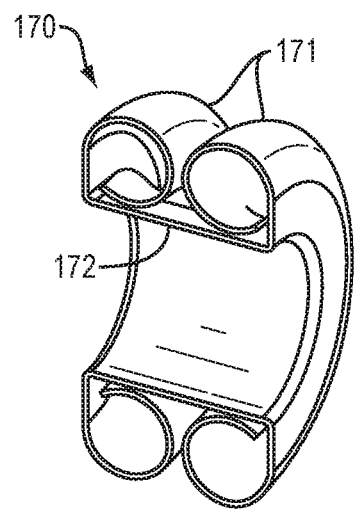

FIGS. 15A-15B are cross-sectional and exterior views, respectively, of a stent 170 in accordance with some embodiments. The flange structures 171 initially project outward away from the stent body and then curl back towards the internal volume of the cylindrical saddle region 172 to form a semi-circular flange configuration. The flange provides additional lateral strength and improved pullout force while minimizing the chance of material or fluid from getting stuck within the internal volume of the flange. FIG. 15C is an alternate configuration with the semi-circular flange structure 171 curled back towards the cylindrical saddle region 172.

Figure 16A:
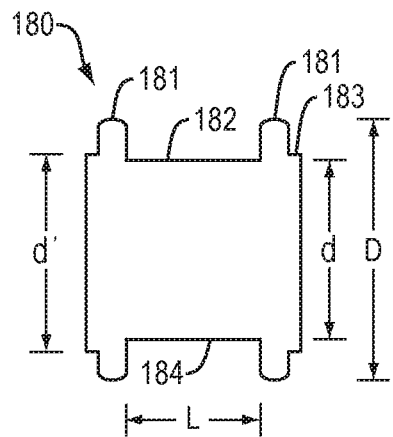
FIG. 16A-16D illustrate cross sections of stents in accordance with some embodiments.
Figure 16B:
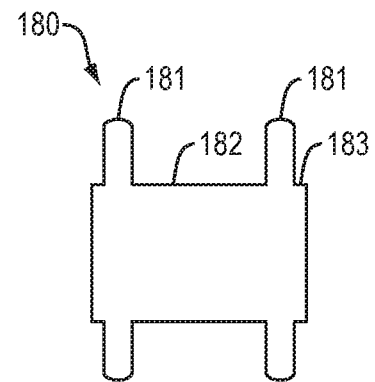
Figure 16C:
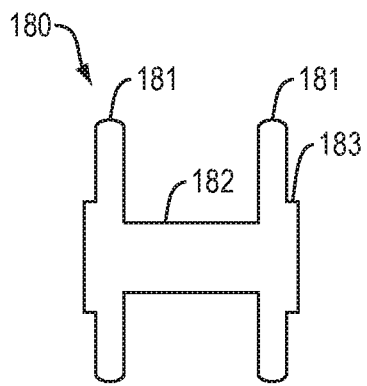

The stent structures shown in FIGS. 16A-16D can be referred to as double-walled flange structures. FIG. 16A illustrates a stent 180 with cylindrical saddle region 182 and a flange 181 with a relatively large open cylindrical region and a wide cuff or lip 183 on the flange structure 181. FIG. 16B illustrates a stent 180 with a smaller internal diameter than FIG. 16A but with a larger double-walled flange 181 for atraumatically engaging the tissue. FIG. 16C illustrates a stent 180 with an outer cuff or lip 183 diameter that is greater than the diameter of the internal cylindrical saddle region.

Figure 16D:
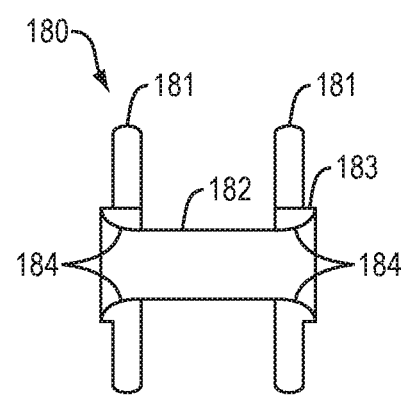

FIG. 16D illustrates an embodiment of a stent 180 similar to FIG. 16C but with a separate plug 184 in the flange 181 to prevent fluid or material from getting stuck in the flange volume. The plug can be made of a material that is suitable to flow or pass through the digestive track after the stent is removed. In some embodiments the flange can be made out of a biodegradable or bioabsorbable material. The flange plug structure can be used with any of the stent structures disclosed herein.

In an exemplary EUS procedure an endoscope with ultrasound capabilities enters the mouth and advances down the esophagus and into the stomach. An ultrasound target can be optionally placed within a target body lumen. There are many methods of creating an ultrasound target, for example an infusion catheter can be used to inject a bolus of saline that can be identified by ultrasound. Ultrasonic guidance is used to advance a needle from the endoscope working channel to initially puncture the stomach wall and the wall target body lumen followed by advancing a guidewire into the target body lumen. A catheter device carrying a stent can follow the guidewire to gain access to the target body lumen. In this embodiment needle access is preferred; however, in some embodiments the catheter can be used to make the initial penetrations in the stomach wall and target body lumen using an energized distal tip directly without the use of a needle and guidewire (such catheter devices are disclosed in application Ser. No. 13/871,978 filed on Apr. 26, 2013 that published as US 2013/0310833 and application Ser. No. 14/186,994). After gaining access to the target body lumen the catheter device can deploy an upstream end of the stent in the target body lumen by withdrawing or retracting a sheath constraining the stent. The downstream end of the stent can then be deployed in the stomach by continuing to retract the sheath constraining the stent. After deploying the stent a pathway is formed through the interior of the stent between the stomach and the target body lumen. The delivery catheter is removed and the stent can be optionally dilated. After deployment of the stent the endoscope is removed. The stent can later be removed endoscopically using a snare or other known technique. Similar techniques can be used with the ERCP procedures with the endoscope positioned in the duodenum.

As noted above any of the stents disclosed herein can be used in ERCP processes. An ERCP procedure can include advancing an endoscope through the mouth and stomach and into the intestines. The endoscope can be advanced to an area of the intestines adjacent to the ampulla of Vater. A guidewire can be advanced from a working channel of the endoscope into the ampulla of Vater and into the common bile duct or pancreatic duct. A catheter carrying a self-expanding stent can be advanced over the guidewire to gain access to the common bile duct or the pancreatic duct. The catheter can retract a sheath to allow the self-expanding stent to expand. The sheath can be retracted partially to allow the first end or upstream end of the stent to expand within the common bile duct or pancreatic duct. After the upstream end has been deployed the sheath can be further retracted to deploy the second or downstream end of the stent. The downstream end of the stent can be deployed in the ampulla of Vater, intestines, or other area of the common bile duct, or pancreatic duct. The cylindrical saddle region of the stent forms a fluid conduit or pathway between the common bile duct or pancreatic duct and the ampulla of Vater, intestines, or other area of the common bile duct, or pancreatic duct.

Figure 11:
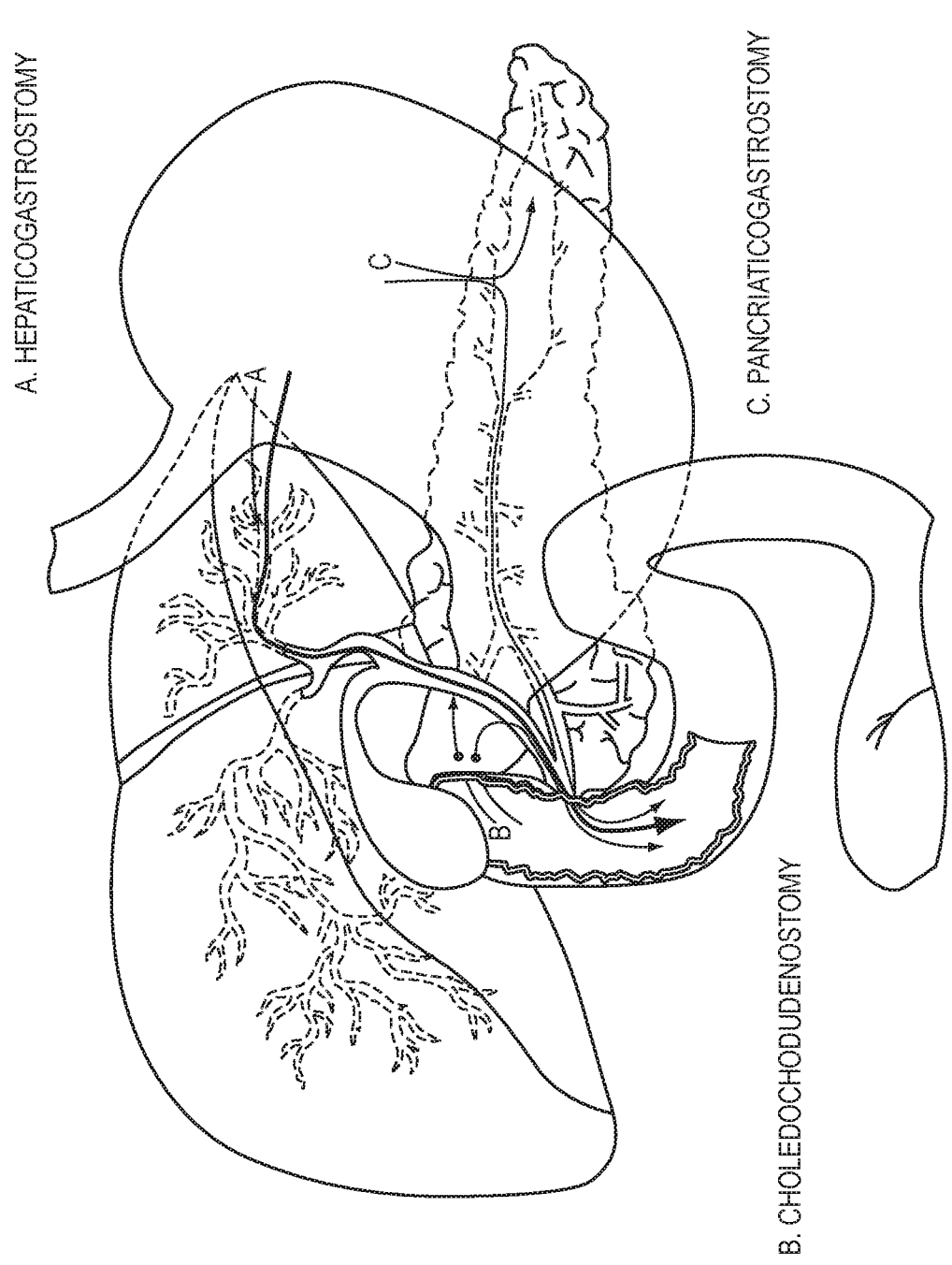
FIG. 11 illustrates a portion of the liver, stomach, duodenum, pancreas, and related anatomy.
Figure 12:
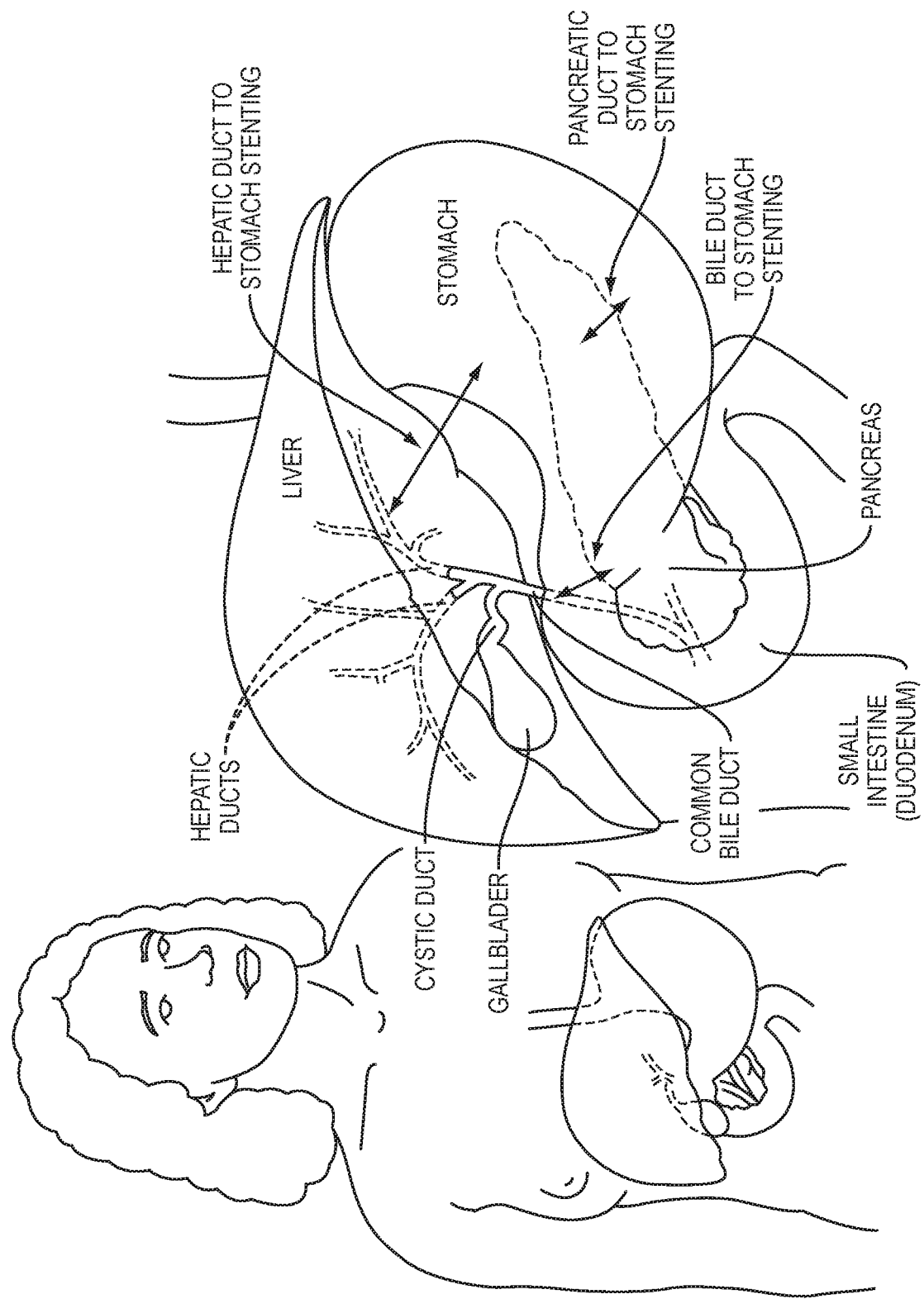
FIG. 12 illustrates a portion of the liver, stomach, duodenum, pancreas, and related anatomy.

FIGS. 11 and 12 illustrate additional examples of body lumens that can be connected by the stents disclosed herein. The arrows on FIGS. 11 and 12 illustrate the area in the abdominal cavity where the stent would span to connect the common bile duct to the duodenum (e.g. FIG. 11, #3) or stomach to various positions in the biliary tree. FIG. 11 and FIG. 12 illustrate the areas in the abdominal cavity where the stent would span between the stomach and duodenum and other areas of the biliary tree.

FIG. 11 illustrates various numbered locations 1-6 where stents can be placed within the abdominal cavity. In some embodiments any of the stents disclosed herein can be placed in any of the locations illustrated in FIGS. 11 and 12. For example, any of the procedures illustrated in FIGS. 11 and 12 can be used instead of an ERCP procedure. In some cases an ERCP procedure can be unsuccessful or not possible, in those cases a stent can be placed through any of the pathways illustrated in FIGS. 11 and 12.

In some embodiments the stents disclosed herein can be used for a choledochodudenostomy as shown in FIG. 11, #3, which connects the common bile duct to the duodenum. For a choledochodudenostomy an endoscope can be advanced through the mouth and stomach and into the duodenum. A target location in the common bile duct can be identified using ultrasound guidance or other methods of guidance. A needle or catheter device can be advanced from the endoscope to puncture the wall of the duodenum and the common bile duct. If a needle is used to access the common bile duct then a guidewire can be placed with a catheter accessing the common bile duct by advancing over the guidewire. The catheter can deploy a stent with an upstream end or flange within the common bile duct and a downstream end or flange deployed in the duodenum thereby forming a fluid conduit between the common bile duct and the duodenum.

In some embodiments the stents disclosed herein can be used for a hepaticogastrostomy, which connects the hepatic duct to the stomach. The arrows in FIGS. 11 (#1) and 12 illustrate the area in the abdominal cavity where the stent would span to connect the hepatic duct to the stomach. An endoscope can be advanced through the mouth and into the stomach. The target location in the liver can be identified using ultrasound guidance or other methods of guidance. A needle or catheter device can be advanced to puncture the stomach and liver. A guidewire can be placed in the liver (after needle access) followed by advancing a catheter carrying a stent over the guidewire. An upstream end of the stent can be placed in the liver and hepatic duct using the catheter. A downstream end of the stent is deployed within the stomach. The stent can have an uncovered portion on the end of the stent that is released inside the liver and hepatic duct. For example, the upstream end that is deployed within the liver can have an uncovered portion of about 3-4 cm. The uncovered portion on the end of the stent can facilitate the flow of bile out of the liver and through the internal volume of the stent to drain to the stomach. The pressure in the liver can assist the drainage of bile from the liver through the stent and into the stomach. The downstream end of the stent deployed in the stomach can be covered to reduce contact between the bile and the wall of the stomach.

Pathway #2 in FIG. 11 illustrates an alternate access pathway for accessing the common bile duct and subsequently placing an intraluminal stent in the common bile duct. In some cases, ERCP can fail about 1% of the time. If the ERCP procedure fails then alternate access to the common bile duct is needed. As illustrated in FIG. 11 #2 the hepatic duct can be accessed by advancing a needle through the stomach and liver wall to puncture the hepatic duct. A guidewire can be subsequently passed through the hepatic duct and common bile duct. The flow of bile can assist the advancement of the guide wire through the common bile duct and into the ampulla of Vater and duodenum. A forceps or other surgical tool can be used to grasp the end of the guidewire in the duodenum. The forceps or other surgical tool can then pull the end of the guidewire out through the patient's mouth. Once the end of the guidewire is out of the patient's body a catheter can be advanced over the guidewire. The catheter can be advanced through the stomach, duodenum, ampulla of Vater, and into the bile duct. After the catheter has access to the common bile duct the steps in an ERCP can be pursued, such as cutting the ampulla of Vater, pulling out stones, addressing strictures, etc. This type of procedure can be referred to as a rendezvous procedure. The catheter can also be used for additional medical procedures as desired, such as placing any of the stents disclosed herein.

Pathway #4 illustrates another type of rendezvous procedure. A needle can be advanced into the duodenum. The bile duct can be located and targeted by the needle. The needle is then advanced through the wall of the duodenum and into the bile duct. A guidewire can then be passed from the needle into the bile duct. The guidewire can be advanced through the bile duct and into the ampulla of Vater and into the duodenum. The guidewire can be grabbed in the duodenum using a forceps or other surgical tool and pulled out through the mouth. Once the end of the guidewire is out of the patient's body a catheter can be advanced over the guidewire. The catheter can be advanced through the stomach and duodenum and into the bile duct. The catheter can then be used for additional medical procedures as desired, such as placing any of the stents disclosed herein.

Pathway #5 illustrates a pathway for a rendezvous procedure through the pancreatic duct. A needle can be advanced into the stomach. The pancreatic duct can be located and targeted by the needle. The needle is then advanced through the wall of the stomach and into the pancreatic duct. A guidewire can then be passed from the needle into the pancreatic duct. The guidewire can be advanced through the pancreatic duct and into the ampulla of Vater and duodenum. The guidewire can be grabbed in the duodenum using a forceps or other surgical tool and pulled out through the mouth. Once the end of the guidewire is out of the patient's body a catheter can be advanced over the guidewire. The catheter can be advanced through the stomach and duodenum and into the pancreatic duct. The catheter can then be used for additional medical procedures as desired, such as placing any of the stents disclosed herein.

In some embodiments the stents disclosed herein can be used for a pancriaticogastrostomy, which connects the pancreatic duct to the stomach. The arrows on FIGS. 11 (#6) and 12 illustrate the area in the abdominal cavity where the stent would span to connect the pancreatic duct to the stomach. For a pancriaticogastrostomy an endoscope can be advanced through the mouth and into the stomach. A target location in the pancreatic duct can be identified using ultrasound guidance or other methods of guidance. A needle or catheter device can be advanced from the endoscope to puncture the wall of the stomach and the pancreatic duct. A guidewire can be placed in the pancreatic duct (after needle access) followed by advancing a catheter carrying a stent over the guidewire. An upstream end of the stent can be placed in the pancreatic duct using the catheter. A downstream end of the stent is deployed within the stomach thereby forming a fluid conduit between the pancreatic duct and the stomach.

In some embodiments the stents disclosed herein can be used to place a stent anterograde. Anterograde stent placement can be done in the bile duct and pancreatic duct. Anterograde stent placement is where the operator enters the upstream part of the bile duct (or pancreatic duct). The upstream part of the bile duct can be accessed percutaneously (e.g. transhepatic) or under EUS-guidance (e.g. transenteric targeting an intra- or extra-hepatic bile duct—see FIG. 11 #2 pathway). After obtaining access to the upstream part of the bile duct, a guide wire is inserted and advanced downstream to cross the stricture and ampulla and advanced into the duodenum. A stent is then advanced anterogradely over the wire to cross the stricture and the ampulla until the downstream end of the stent is in the duodenum. The sheath is retracted relative to the stent to release the downstream flange or double-walled flange. The sheath and stent can then be retracted as a single unit until the flange abuts against the ampulla of Vater, signaled by the resistance encountered with retraction. The sheath is then retracted relative to the stent to deploy the upstream flange inside the bile duct. A similar procedure can be used to place a stent anterograde in the pancreatic duct (see FIG. 11 #5 pathway) after obtaining upstream access to the pancreatic duct.

According to additional aspects of the present disclosure, a bi-flanged ERCP stent, which may be shorter than those previously described herein, may be temporarily inserted into the lower end of the common bile duct to allow for easier passage of endoscopes into the bile duct. Such an arrangement can enable easy insertion of a cholangioscope into the bile or pancreatic duct for cholangioscopy or pancreatoscopy ("ductoscopy"). Entering the ducts is typically very difficult due to sharp angulation of the ducts relative to duodenum, i.e. axes of the ducts are 90-degrees to that of duodenum. The temporary stent allows the scope to engage the opening of stent rather than the duct opening directly, and stabilizes the scope for advancement into the duct.

For the above ductoscopy, a short stent can be used since there is no stricture to bridge, only the ampulla/sphincter of Oddi. The stent diameter may be 8 mm to enable insertion of an ultra-slim gastroscope (6 mm diameter, for example). After inserting the stent, the duodenoscope may be removed and replaced with a 'transnasal' gastroscope. This scope is longer than a standard gastroscope, but inserted per orally. This procedure may be referred to as 'direct per oral cholangioscopy'. Immediately after the ductoscopy is performed, the stent may be removed.

The short ERCP stent may also be suited for treatment of 'sphincter of Oddi dyskinesia'. This is a condition where the sphincter is in constant spasm, causing increased bile duct pressures and consequently pain. Even after sphincterotomy, the ampullary opening scars down and impedes bile flow, continuing to cause pain.

While the above is a complete description of exemplary embodiments of the present disclosure, various alternatives, modifications, and equivalents may be used. Therefore, the above description should not be taken as limiting the scope of the disclosure, which is defined by the appended claims and the claims in any subsequent applications claiming priority hereto.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A stent, comprising:
   a body having an elongated tubular configuration and a foreshortened configuration,
   wherein a downstream end of the body expands into a downstream flange structure, and an upstream end of the body expands into a flared flange structure,
   wherein the flared flange structure includes a ramped portion and a cylindrical portion,
   wherein a cylindrical saddle region extends between the downstream flange structure and the flared flange structure, and
   wherein the ramped portion of the flared flange structure includes an axial length at least as long as a maximum diameter of the cylindrical saddle region when the body is in the foreshortened configuration.

2. The stent of claim 1, wherein the cylindrical portion of the flared flange structure is substantially parallel to the cylindrical saddle region.

3. The stent of claim 1, wherein the flared flange structure comprises a larger maximum lateral diameter than that of the downstream flange structure when the body is in the foreshortened configuration.

4. The stent of claim 1, wherein the flared flange structure comprises a larger maximum axial width than that of the downstream flange structure when the body is in the foreshortened configuration.

5. The stent of claim 1, wherein the flared flange structure comprises both a larger maximum lateral diameter and a larger maximum axial width than those of the downstream flange structure when the body is in the foreshortened configuration.

6. The stent of claim 1, where at least a portion the flared flange structure is uncovered and the downstream flange structure is covered.

7. A stent comprising;
   a body having an elongated tubular configuration and a foreshortened configuration,
   wherein a downstream end of the body expands into a double-wall flange structure, and an upstream end of the body expands into a flared flange structure,
   wherein the flared flange structure includes a ramped portion and a cylindrical portion, and
   wherein an axial width of the cylindrical portion is greater than an axial width of the double-wall flange structure.

8. The stent of claim 7, further comprising a cylindrical saddle region extending between the double-wall flange structure and the flared flange structure, and wherein the cylindrical portion of the flared flange structure is substantially parallel to the cylindrical saddle region.

9. The stent of claim 7, wherein an axial width of a distal portion of the ramped portion is greater than an axial width of the double-wall flange structure.

10. The stent of claim 8, wherein the double-wall flange structure, the cylindrical saddle region and the cylindrical portion of the flared flange structure comprises a covered mesh, and the ramped portion of the flared flange structure comprises an uncovered mesh.

11. A method, comprising:
   advancing a stent into a first body lumen, wherein the stent includes an elongated tubular configuration and a foreshortened configuration, wherein a downstream end of the body expands into a downstream flange structure, and an upstream end of the body expands into a flared flange structure, wherein the flared flange structure includes a ramped portion and a cylindrical portion;
   advancing the stent into a second body lumen through an opening in the first body lumen;
   expanding the upstream end of the body into the flared flange structure within the second body lumen; and
   expanding the downstream end of the body into the downstream flange structure within the first body lumen.

12. The method of claim 11, wherein at least the cylindrical portion of the flared flange structure contacts a wall of the second body lumen.

13. The method of claim 11, wherein a surface of the downstream flange structure contacts a wall of the second body lumen.

14. The method of claim 11, wherein the downstream flange structure is configured with a double-wall.

15. The method of claim 11, wherein the first body lumen is a duodenum and the second body lumen is a common bile duct.

16. A stent, comprising:
   a body having an elongated tubular configuration and a foreshortened configuration,
   wherein a downstream end of the body expands into a double-wall flange structure, an upstream end of the body expands into a flared flange structure, and a cylindrical saddle region extends between the double-wall flange structure and the flared flange structure, wherein the flared flange structure includes a ramped portion and a cylindrical portion, and wherein an axial width of a distal portion of the ramped portion is greater than an axial width of the double-wall flange structure.

17. The stent of claim 16, wherein the ramped portion of the flared flange structure includes an axial length at least as long as a maximum diameter of the cylindrical saddle region when the body is in the foreshortened configuration.

18. The stent of claim 16, wherein the flared flange structure comprises a distal-most opening having a diameter larger than a maximum internal diameter of the cylindrical saddle region when the body is in the foreshortened configuration.

19. The stent of claim 16, wherein the double-wall flange structure, the cylindrical saddle region and the cylindrical portion of the flared flange structure comprises a covered mesh, and the ramped portion of the flared flange structure comprises an uncovered mesh.

20. The stent of claim 16, wherein an axial width of the cylindrical portion is greater than an axial width of the double-wall flange structure.

* * * * *